US 6,575,994 B1

(12) United States Patent
Marin et al.

(10) Patent No.: US 6,575,994 B1
(45) Date of Patent: *Jun. 10, 2003

(54) METHOD AND APPARATUS CONCERNING BYPASS GRAFTS

(75) Inventors: Michael L. Marin, New York, NY (US); Ralph Marin, New York, NY (US)

(73) Assignee: Teramed, Inc.

(*) Notice: Subject to any disclaimer, the term of this patent is extended or adjusted under 35 U.S.C. 154(b) by 0 days.

This patent is subject to a terminal disclaimer.

(21) Appl. No.: 09/709,798

(22) Filed: Nov. 10, 2000

Related U.S. Application Data

(63) Continuation of application No. 09/504,732, filed on Feb. 16, 2000, now Pat. No. 6,168,610, which is a continuation of application No. 08/838,126, filed on Apr. 15, 1997, now Pat. No. 6,039,749, which is a continuation of application No. 08/537,630, filed on Oct. 2, 1995, now Pat. No. 5,695,517, which is a division of application No. 08/324,893, filed on Oct. 18, 1994, now Pat. No. 5,507,764, which is a continuation-in-part of application No. 08/196,278, filed on Feb. 10, 1994, now Pat. No. 5,443,477.

(51) Int. Cl.$^7$ ............................................. A61B 17/00
(52) U.S. Cl. ..................................................... 606/198
(58) Field of Search ............................... 606/108, 194, 606/198, 200; 623/1.23, 1.32, 1.35, 1.36, 1.49, 1.51, 1.1, 1.11

(56) References Cited

U.S. PATENT DOCUMENTS

| 3,585,707 A | 6/1971 | Stevens |
| 3,657,744 A | 4/1972 | Ersek |
| 4,169,464 A | 10/1979 | Obrez |
| 4,187,390 A | 2/1980 | Gore |

(List continued on next page.)

FOREIGN PATENT DOCUMENTS

| DE | 3205942 A1 | 9/1983 |
| DE | 4130431 | 3/1993 |
| EP | 0554082 | 1/1993 |
| EP | 0 540 290 A3 | 5/1993 |
| EP | 0551179 | 7/1993 |
| EP | 0579523 A1 | 1/1994 |
| EP | 0657147 A2 | 10/1994 |
| EP | 0686379 B1 | 12/1995 |
| EP | 734698 A2 | 10/1996 |
| EP | 783873 A2 | 7/1997 |
| EP | 800801 A1 | 10/1997 |
| EP | 830853 A1 | 3/1998 |

(List continued on next page.)

OTHER PUBLICATIONS

Chuter, T.A.M., et al., "Transfemoral endovascular aortic graft placement", Journal of Vascular Surgery, vol. 18, No. 2, pp. 185–197.
Brody, J.E. "Aneurysm: a potential killer lurking in the aorta", The New York Times, Health Section, pp. C14–15.
Parodi, J.C., "Transfemoral Intraluminal Graft Implantation for Abdominal Aortic Aneurysms", Annals of Vascular Surgery, vol. 5, No. 6, 1991, pp. 491–9.
PCT/US 95/12582, Feb. 1996, International Search Report.

*Primary Examiner*—John J. Wilson
*Assistant Examiner*—Melba Bumgarner

(57) ABSTRACT

Disclosed is a method for excluding a pathological defect such as an aortic aneurysm. By the disclosed method, a grafstent complex is advanced through each branch of the patient's femoral and iliac system. The graftstent complex includes a segment of prosthetic graft material attached at each end to a respective stent. The cephalic stents of each graftstent complex are positioned relative to one other in a common region of normal aortic tissue on one side of the aneurysm and then deployed. The caudal stents are deployed in the iliac arteries. Additional steps can be taken to ensure that the internal iliac artery is not blocked when the caudal stents are deployed.

7 Claims, 14 Drawing Sheets

U.S. PATENT DOCUMENTS

| | | |
|---|---|---|
| 4,317,451 A | 3/1982 | Cerwin et al. |
| 4,441,216 A | 4/1984 | Ionescu et al. |
| RE31,618 E | 7/1984 | Mano et al. |
| 4,503,569 A | 3/1985 | Dotter |
| 4,553,545 A | 11/1985 | Maass et al. |
| 4,562,596 A | 1/1986 | Kornberg |
| 4,580,568 A | 4/1986 | Gianturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes et al. |
| 4,731,073 A | 3/1988 | Robinson |
| 4,732,152 A | 3/1988 | Wallsten et al. |
| 4,733,665 A | 3/1988 | Palmaz |
| 4,739,762 A | 4/1988 | Palmaz |
| 4,762,128 A | 8/1988 | Rosenbluth |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 4,856,516 A | 8/1989 | Hillstead |
| 4,875,480 A | 10/1989 | Imbert |
| 4,886,062 A | 12/1989 | Wiktor |
| 4,907,336 A | 3/1990 | Gianturco |
| 4,913,141 A | 4/1990 | Hillstead |
| 4,925,445 A | 5/1990 | Sakamoto et al. |
| 4,950,227 A | 8/1990 | Savin et al. |
| 4,955,899 A | 9/1990 | Della Corna et al. |
| 4,969,458 A | 11/1990 | Wiktor |
| 4,983,167 A | 1/1991 | Sahota |
| 4,990,131 A | 2/1991 | Dardik et al. |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton et al. |
| 5,035,694 A | 7/1991 | Kasprzyk et al. |
| 5,035,706 A | 7/1991 | Gianturco et al. |
| 5,041,126 A | 8/1991 | Gianturco |
| 5,045,072 A | 9/1991 | Castillo et al. |
| 5,064,435 A | 11/1991 | Porter |
| 5,078,726 A | 1/1992 | Kreamer |
| 5,084,065 A | 1/1992 | Weldon et al. |
| 5,100,422 A | 3/1992 | Berguer et al. |
| 5,102,417 A | 4/1992 | Palmaz |
| 5,104,399 A | 4/1992 | Lazarus |
| 5,104,400 A | 4/1992 | Berguer et al. |
| 5,104,404 A | 4/1992 | Wolff |
| 5,114,423 A | 5/1992 | Kasprzyk et al. |
| 5,116,365 A | 5/1992 | Hillstead |
| 5,122,154 A * | 6/1992 | Rhodes ........................ 606/198 |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi et al. |
| 5,156,620 A | 10/1992 | Pigott |
| 5,159,920 A | 11/1992 | Condon et al. |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Hull |
| 5,192,307 A | 3/1993 | Wall |
| 5,195,984 A | 3/1993 | Schatz |
| 5,197,978 A | 3/1993 | Hess |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi et al. |
| 5,222,971 A | 6/1993 | Willard et al. |
| 5,236,447 A | 8/1993 | Kubo et al. |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno et al. |
| 5,290,305 A | 3/1994 | Inoue |
| 5,292,331 A | 3/1994 | Boneau |
| 5,304,197 A | 4/1994 | Pinchuk et al. |
| 5,304,200 A | 4/1994 | Spaulding |
| 5,304,220 A | 4/1994 | Maginot |
| 5,306,294 A | 4/1994 | Winston et al. |
| 5,314,444 A | 5/1994 | Gianturco |
| 5,314,472 A | 5/1994 | Fontaine |
| 5,316,023 A | 5/1994 | Palmaz et al. |
| 5,318,535 A | 6/1994 | Miraki |
| 5,321,109 A | 6/1994 | Bosse et al. |
| 5,330,490 A | 7/1994 | Wilk et al. |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone et al. |
| 5,366,473 A | 11/1994 | Winston et al. |
| 5,366,504 A | 11/1994 | Andersen et al. |
| 5,370,683 A | 12/1994 | Fontaine |
| 5,370,691 A | 12/1994 | Samson |
| 5,375,612 A * | 12/1994 | Cottenceau et al. ........ 606/200 |
| 5,376,112 A | 12/1994 | Duran |
| 5,380,328 A | 1/1995 | Morgan |
| 5,382,261 A | 1/1995 | Palmaz |
| 5,383,892 A | 1/1995 | Cardon et al. |
| 5,383,927 A | 1/1995 | De Goicoechea et al. |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Solar |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,453,090 A | 9/1995 | Martinez et al. |

| Patent No. | Date | Inventor |
|---|---|---|
| 5,453,235 A | 9/1995 | Calcote et al. |
| 5,456,713 A | 10/1995 | Chuter |
| 5,466,509 A | 11/1995 | Kowligi et al. |
| 5,468,138 A | 11/1995 | Bosse et al. |
| 5,476,506 A | 12/1995 | Lunn |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,496,365 A | 3/1996 | Fontaine et al. |
| 5,507,767 A | 4/1996 | Maeda et al. |
| 5,507,769 A | 4/1996 | Marin et al. |
| 5,507,771 A | 4/1996 | Gianturco |
| 5,507,995 A | 4/1996 | Schweich, Jr. et al. |
| 5,512,229 A | 4/1996 | Bosse et al. |
| 5,522,880 A | 6/1996 | Barone et al. |
| 5,522,882 A | 6/1996 | Gaterud et al. |
| 5,527,354 A | 6/1996 | Fontaine et al. |
| 5,549,662 A | 8/1996 | Fordenbacher |
| 5,549,663 A | 8/1996 | Cottone, Jr. |
| 5,562,698 A | 10/1996 | Parker |
| 5,562,724 A | 10/1996 | Vorwerk et al. |
| 5,562,726 A * | 10/1996 | Chuter ................. 606/195 |
| 5,569,295 A | 10/1996 | Lam |
| 5,571,170 A | 11/1996 | Palmaz et al. |
| 5,571,171 A | 11/1996 | Barone et al. |
| 5,571,173 A | 11/1996 | Parodi |
| 5,578,071 A | 11/1996 | Parodi |
| 5,578,072 A | 11/1996 | Barone et al. |
| 5,591,196 A | 1/1997 | Marin et al. |
| 5,591,197 A | 1/1997 | Orth et al. |
| 5,591,228 A | 1/1997 | Edoga |
| 5,591,229 A | 1/1997 | Parodi |
| 5,593,412 A | 1/1997 | Martinez et al. |
| 5,607,444 A | 3/1997 | Lam |
| 5,607,464 A | 3/1997 | Trescony et al. |
| 5,609,624 A | 3/1997 | Kalis |
| 5,609,625 A | 3/1997 | Piplani et al. |
| 5,609,627 A | 3/1997 | Goicoechea et al. |
| 5,617,878 A | 4/1997 | Taheri |
| 5,618,300 A | 4/1997 | Marin et al. |
| 5,628,783 A | 5/1997 | Quiachon et al. |
| 5,628,786 A | 5/1997 | Banas et al. |
| 5,628,788 A | 5/1997 | Pinchuk |
| 5,632,763 A | 5/1997 | Glastra |
| 5,632,778 A | 5/1997 | Goldstein |
| 5,639,278 A | 6/1997 | Dereume et al. |
| 5,641,443 A | 6/1997 | Calcote et al. |
| 5,643,312 A | 7/1997 | Fischell et al. |
| 5,645,559 A | 7/1997 | Hachtman et al. |
| 5,649,952 A | 7/1997 | Lam |
| 5,653,743 A | 8/1997 | Martin |
| 5,653,745 A | 8/1997 | Trescony et al. |
| 5,653,747 A | 8/1997 | Dereume |
| 5,662,700 A | 9/1997 | Lazarus |
| 5,662,703 A | 9/1997 | Yurek et al. |
| 5,667,523 A | 9/1997 | Bynon et al. |
| 5,669,924 A | 9/1997 | Shaknovich |
| 5,669,936 A | 9/1997 | Lazarus |
| 5,674,241 A | 10/1997 | Bley et al. |
| 5,674,276 A | 10/1997 | Andersen et al. |
| 5,676,696 A | 10/1997 | Marcade |
| 5,676,697 A | 10/1997 | McDonald |
| 5,681,345 A | 10/1997 | Euteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,685,847 A | 11/1997 | Barry |
| 5,693,083 A | 12/1997 | Baker et al. |
| 5,693,084 A | 12/1997 | Chuter |
| 5,693,085 A | 12/1997 | Buirge et al. |
| 5,693,086 A | 12/1997 | Goicoechea et al. |
| 5,695,517 A | 12/1997 | Marin et al. |
| 5,697,948 A | 12/1997 | Marin et al. |
| 5,697,971 A | 12/1997 | Fischell et al. |
| 5,700,285 A | 12/1997 | Myers et al. |
| 5,702,418 A | 12/1997 | Ravenscroft |
| 5,713,917 A | 2/1998 | Leonhardt et al. |
| 5,716,365 A | 2/1998 | Goicoechea et al. |
| 5,718,159 A | 2/1998 | Thompson |
| 5,718,724 A | 2/1998 | Goicoechea et al. |
| 5,720,735 A | 2/1998 | Dorros |
| 5,720,776 A | 2/1998 | Chuter et al. |
| 5,723,003 A | 3/1998 | Winston et al. |
| 5,723,004 A | 3/1998 | Dereume et al. |
| 5,725,534 A | 3/1998 | Rasmussen |
| 5,725,568 A | 3/1998 | Hastings |
| 5,725,570 A | 3/1998 | Heath |
| 5,728,065 A | 3/1998 | Follmer et al. |
| 5,728,068 A | 3/1998 | Leone et al. |
| 5,728,131 A | 3/1998 | Frantzen et al. |
| 5,733,328 A | 3/1998 | Fordenbacher |
| 5,735,892 A | 4/1998 | Myers et al. |
| 5,746,709 A | 5/1998 | Rom et al. |
| 5,749,880 A | 5/1998 | Banas et al. |
| 5,749,920 A | 5/1998 | Quiachon et al. |
| 5,749,921 A | 5/1998 | Lenker et al. |
| 5,752,966 A | 5/1998 | Chang |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,772 A | 5/1998 | Evans et al. |
| 5,755,773 A | 5/1998 | Evans et al. |
| 5,755,777 A | 5/1998 | Chuter |
| 5,758,562 A | 6/1998 | Thompson |
| 5,760,006 A | 6/1998 | Shank et al. |
| 5,766,201 A | 6/1998 | Ravenscroft et al. |
| 5,769,882 A | 6/1998 | Fogarty et al. |
| 5,769,885 A | 6/1998 | Quiachon et al. |
| 5,776,180 A | 7/1998 | Goicoechea et al. |
| 5,782,765 A | 7/1998 | Jonkman |
| 5,782,906 A | 7/1998 | Marshall et al. |
| 5,782,909 A | 7/1998 | Quiachon et al. |
| 5,788,626 A | 8/1998 | Thompson |
| 5,797,953 A | 8/1998 | Tekulve |
| 5,800,456 A | 9/1998 | Maeda et al. |
| 5,800,508 A | 9/1998 | Goicoechea et al. |
| 5,800,516 A | 9/1998 | Fine et al. |
| 5,800,518 A | 9/1998 | Piplani et al. |
| 5,800,520 A | 9/1998 | Fogarty et al. |
| 5,810,870 A | 9/1998 | Myers et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,043 A | 10/1998 | Cottone, Jr. |
| 5,824,044 A | 10/1998 | Quiachon et al. |
| 5,824,046 A | 10/1998 | Smith et al. |
| 5,824,054 A | 10/1998 | Khosravi et al. |
| 5,824,055 A | 10/1998 | Spiridigliozzi et al. |
| 5,827,310 A | 10/1998 | Marin et al. |
| 5,827,320 A | 10/1998 | Richter et al. |
| 5,827,327 A | 10/1998 | McHaney et al. |
| 5,830,229 A | 11/1998 | Konya et al. |
| 5,833,651 A | 11/1998 | Donovan et al. |
| 5,840,011 A | 11/1998 | Landgrebe et al. |
| 5,843,031 A | 12/1998 | Hermann et al. |
| 5,843,120 A | 12/1998 | Israel et al. |
| 5,843,158 A | 12/1998 | Lenker et al. |
| 5,843,160 A | 12/1998 | Rhodes |
| 5,855,598 A | 1/1999 | Pinchuk |
| 5,857,998 A | 1/1999 | Barry |
| 5,858,556 A | 1/1999 | Eckert et al. |
| 5,860,998 A | 1/1999 | Robinson et al. |
| 5,861,027 A | 1/1999 | Trapp |
| 5,868,777 A | 2/1999 | Lam |
| 5,871,537 A | 2/1999 | Holman et al. |
| 5,871,538 A | 2/1999 | Dereume |

| | | |
|---|---|---|
| 5,876,397 A | 3/1999 | Edelman et al. |
| 5,893,868 A | 4/1999 | Hanson et al. |
| 5,893,887 A | 4/1999 | Jayaraman |
| 5,899,890 A | 5/1999 | Chiang et al. |
| 5,902,308 A | 5/1999 | Murphy |
| 5,904,713 A | 5/1999 | Leschinsky |
| 5,906,619 A | 5/1999 | Olson et al. |
| 5,906,640 A | 5/1999 | Penn et al. |
| 5,906,641 A | 5/1999 | Thompson et al. |
| 5,908,448 A | 6/1999 | Roberts et al. |
| 5,916,263 A | 6/1999 | Goicoechea et al. |
| 5,916,264 A | 6/1999 | Von Oepen et al. |
| 5,919,224 A | 7/1999 | Thompson et al. |
| 5,928,260 A | 7/1999 | Chin et al. |
| 5,935,667 A | 8/1999 | Calcote et al. |
| 5,938,696 A | 8/1999 | Goicoechea et al. |
| 5,944,726 A | 8/1999 | Blaeser et al. |
| 5,944,750 A | 8/1999 | Tanner et al. |
| 5,951,599 A | 9/1999 | McCrory |
| 5,954,693 A | 9/1999 | Barry |
| 5,957,973 A | 9/1999 | Quiachon et al. |
| 5,957,974 A | 9/1999 | Thompson et al. |
| 5,961,546 A * | 10/1999 | Robinson et al. .......... 623/1.23 |
| 5,961,548 A | 10/1999 | Shmulewitz |
| 5,968,069 A | 10/1999 | Dusbabek et al. |
| 5,968,088 A | 10/1999 | Hansen et al. |
| 5,980,565 A | 11/1999 | Jayaraman |
| 5,993,481 A | 11/1999 | Marcade et al. |
| 6,007,543 A | 12/1999 | Ellis et al. |
| 6,015,431 A | 1/2000 | Thornton et al. |
| 6,015,432 A | 1/2000 | Rakos et al. |
| 6,016,810 A | 1/2000 | Ravenscroft |
| 6,017,363 A | 1/2000 | Hojeibane |
| 6,017,364 A | 1/2000 | Lazarus |
| 6,019,778 A | 2/2000 | Wilson et al. |
| 6,019,786 A | 2/2000 | Thompson |
| 6,024,763 A | 2/2000 | Lenker et al. |
| 6,027,526 A | 2/2000 | Limon et al. |
| 6,027,529 A | 2/2000 | Roychowdhury et al. |
| 6,030,413 A | 2/2000 | Lazarus |
| 6,030,415 A | 2/2000 | Chuter |
| 6,033,435 A | 3/2000 | Penn et al. |
| 6,036,697 A | 3/2000 | DiCaprio |
| 6,036,723 A | 3/2000 | Anidjar et al. |
| 6,036,725 A | 3/2000 | Avellanet |
| 6,039,749 A | 3/2000 | Marin et al. |
| 6,039,758 A | 3/2000 | Quiachon et al. |
| 6,048,356 A | 4/2000 | Ravenscroft et al. |
| 6,051,020 A | 4/2000 | Goicoechea et al. |
| 6,056,775 A | 5/2000 | Borghi et al. |
| 6,059,821 A | 5/2000 | Anidjar et al. |
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,077,273 A | 6/2000 | Euteneuer et al. |
| 6,078,832 A | 6/2000 | Lenker et al. |
| 6,086,577 A | 7/2000 | Ken et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,093,199 A | 7/2000 | Brown et al. |
| 6,097,978 A | 8/2000 | Demarais et al. |
| 6,099,558 A | 8/2000 | White et al. |
| 6,099,560 A | 8/2000 | Penn et al. |
| 6,102,938 A | 8/2000 | Evans et al. |
| 6,102,942 A | 8/2000 | Ahari |
| 6,110,191 A | 8/2000 | Dehdashtian et al. |
| 6,110,198 A | 8/2000 | Fogarty et al. |
| 6,117,117 A | 9/2000 | Mauch |
| 6,117,156 A | 9/2000 | Richter et al. |
| 6,117,157 A | 9/2000 | Tekulve |
| 6,117,167 A | 9/2000 | Goicoechea et al. |
| 6,123,722 A | 9/2000 | Fogarty et al. |
| 6,126,685 A | 10/2000 | Lenker et al. |
| 6,129,754 A | 10/2000 | Kanesaka et al. |
| 6,132,450 A | 10/2000 | Hanson et al. |
| 6,132,459 A | 10/2000 | Piplani et al. |
| 6,168,610 B1 * | 1/2001 | Marin et al. ............... 606/1.11 |
| 6,302,906 B1 | 10/2001 | Goicoechea et al. |

FOREIGN PATENT DOCUMENTS

| | | |
|---|---|---|
| EP | 832616 A1 | 4/1998 |
| EP | 0855170 A2 | 7/1998 |
| EP | 880948 A1 | 12/1998 |
| EP | 0928606 A1 | 7/1999 |
| EP | 937442 A2 | 8/1999 |
| EP | 0947179 A2 | 10/1999 |
| EP | 1000590 A1 | 5/2000 |
| FR | 2733682 A1 | 11/1996 |
| FR | 2740346 A1 | 4/1997 |
| FR | 2743293 A1 | 7/1997 |
| GB | 0 662 307 A2 | 9/1948 |
| GB | 1205743 | 9/1970 |
| JP | 5524095 A | 2/1980 |
| JP | 60220030 A | 11/1985 |
| JP | 62231657 A | 3/1988 |
| JP | 464367 A | 2/1992 |
| JP | 4263852 A | 4/1992 |
| JP | 5 76603 A | 3/1993 |
| JP | 5 269199 A | 10/1993 |
| JP | 7529 A | 10/1994 |
| JP | 6282730 A | 10/1994 |
| JP | 7 24072 A | 1/1995 |
| JP | 7100210 A | 4/1995 |
| JP | 6 86827 A | 6/1998 |
| RU | 1680055 A1 | 5/1988 |
| WO | 8704935 A1 | 8/1987 |
| WO | 9516406 A1 | 6/1995 |
| WO | 9521592 A1 | 8/1995 |
| WO | 9626689 A1 | 9/1996 |
| WO | 96/34580 A1 | 11/1996 |
| WO | 9724081 A1 | 7/1997 |
| WO | 9725000 A1 | 7/1997 |
| WO | 9733532 A2 | 9/1997 |
| WO | 9807389 A1 | 2/1998 |
| WO | 98/19628 A1 | 5/1998 |
| WO | 9823322 A1 | 6/1998 |
| WO | 9836709 A1 | 8/1998 |
| WO | 9853761 A1 | 12/1998 |
| WO | 9908744 A1 | 2/1999 |
| WO | 9911199 A1 | 3/1999 |

* cited by examiner

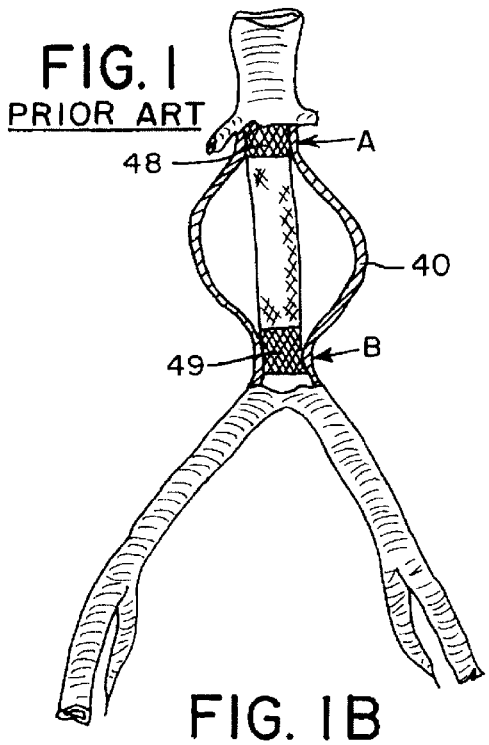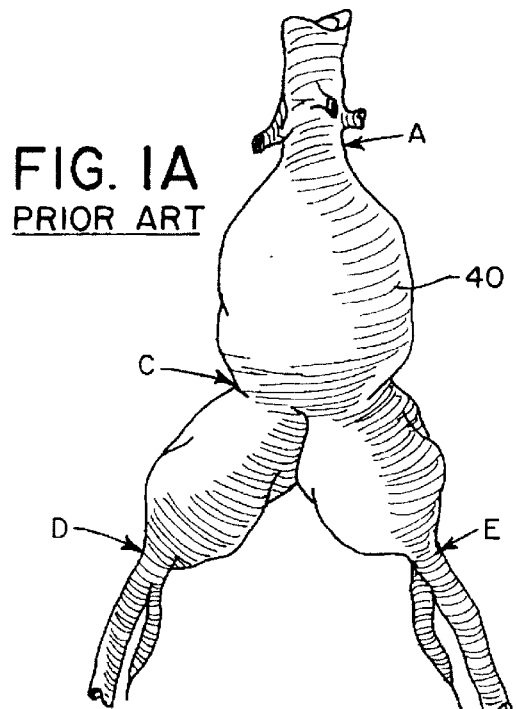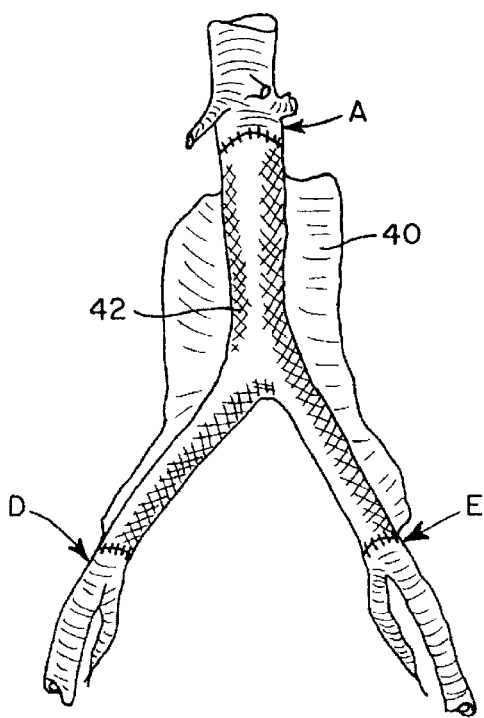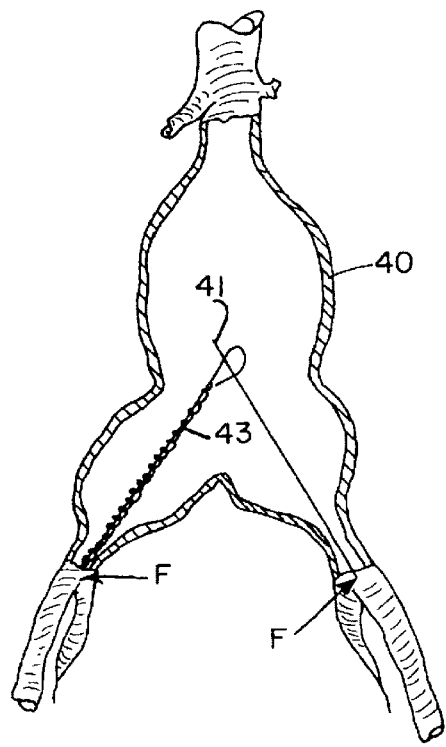

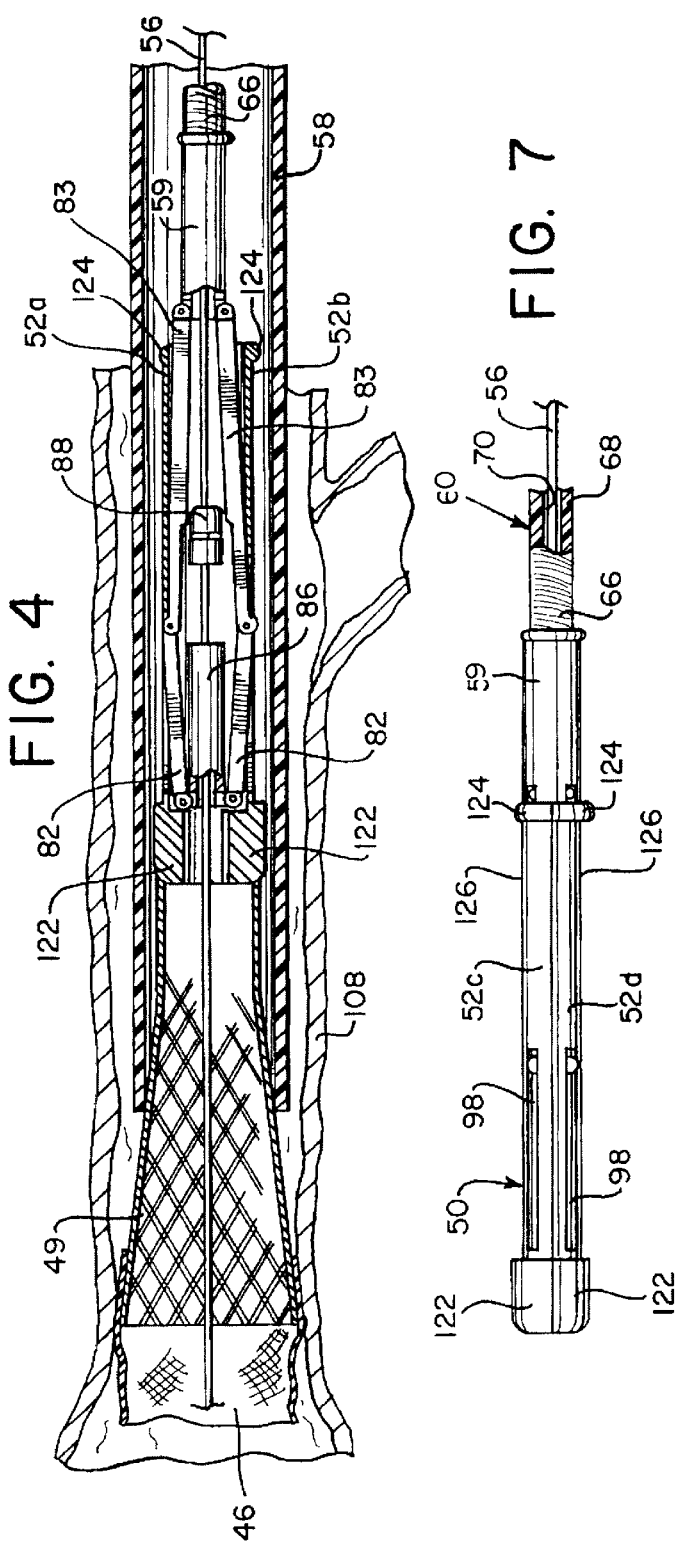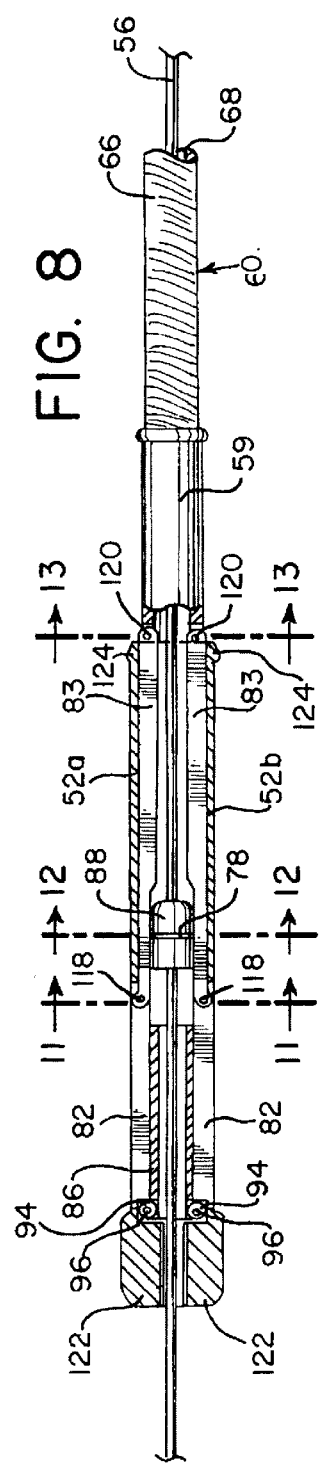

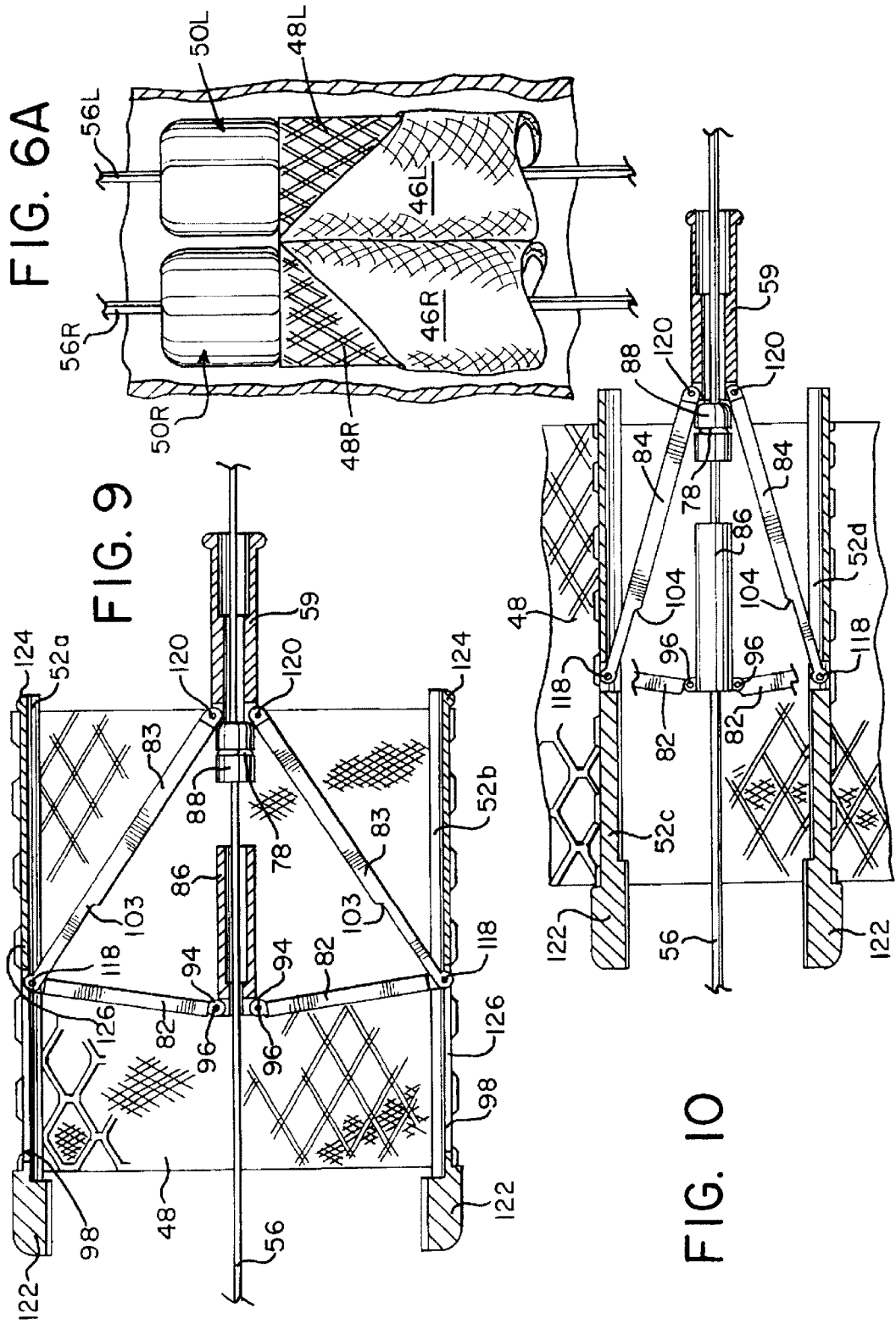

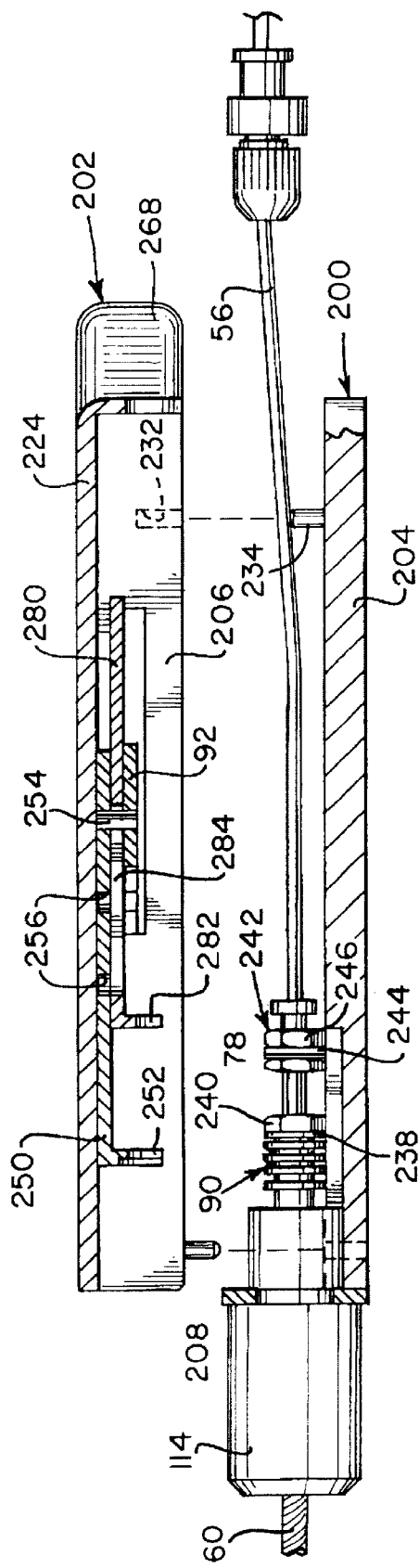
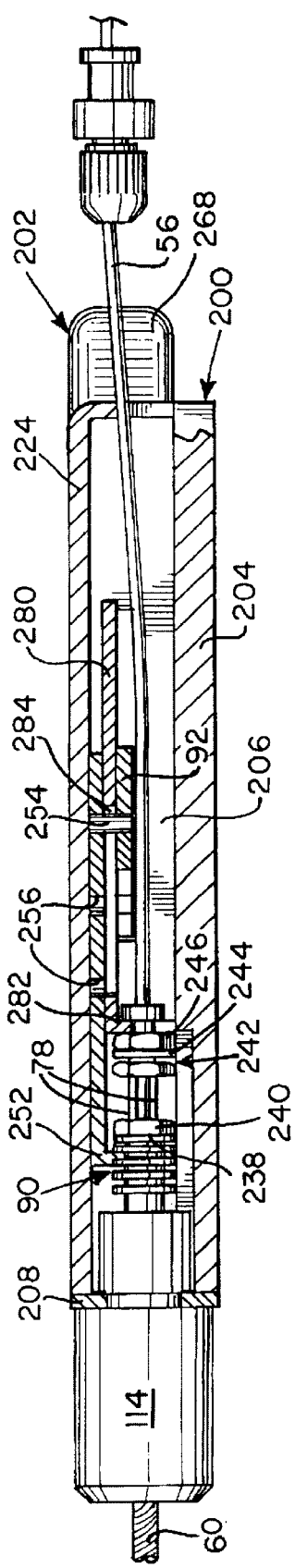
FIG. 18
FIG. 19

METHOD AND APPARATUS CONCERNING BYPASS GRAFTS

RELATED CASES

This is a continuation of application Ser. No. 09/504,732, filed Feb. 16, 2000, now U.S. Pat. No. 6,168,610, which is a continuation of application Ser. No. 08/838,126, filed Apr. 15, 1997, now U.S. Pat. No. 6,039,749, which is a continuation of application Ser. No. 08/537,630, filed Oct. 2, 1995, now U.S. Pat. No. 5,695,517, which is a division of application Ser. No. 08/324,893, filed Oct. 18, 1994, now U.S. Pat. No. 5,507,769, which is a continuation-in-part of U.S. application Ser. No. 08/196,278 for APPARATUS AND METHOD FOR DEPLOYMENT OF RADIALLY EXPANDABLE STENTS BY A MECHANICAL LINKAGE, filed Feb. 10, 1994, now U.S. Pat. No. 5,443,477.

FIELD OF THE INVENTION

The present invention relates to a method and apparatus for endoluminally deploying a graft across an aneurysm and, more particularly, to a catheterization method and apparatus for forming an endoluminal bifurcated graft, such as may be placed across an aortic aneurysm and any associated common iliac aneurysms.

BACKGROUND OF THE INVENTION

Aortic aneurysms represent a significant medical problem for the general population. Aneurysms within the aorta presently affect between two and seven percent of the general population and the rate of incidence appears to be increasing. This form of atherosclerotic vascular disease (hardening of the arteries) is characterized by a degeneration in the arterial wall in which the wall weakens and balloons outward by thinning. An abdominal aortic aneurysm is a dilatation of the main artery of the body. Until the affected artery is removed or bypassed, a patient with an abdominal aortic aneurysm ("AAA") must live with the threat of aortic aneurysm rupture and death. See Brody, J. E., "Aneurysm: A Potential Killer Lurking in the Aorta," *The New York Times*, Apr. 13, 1994, at C14.

One known clinical approach for patients with an abdominal aortic aneurysm is a surgical repair procedure. This is an extensive operation involving transperitoneal or retroperitoneal dissection of the aorta and replacement of the aneurysm with an artificial artery known as a prosthetic graft. This procedure requires a significant abdominal incision extending from the lower border of the breast bone down to the pubic bone to expose the abdominal aorta and the aneurysm so that the graft can be directly implanted. The operation requires a general anesthesia with a breathing tube, extensive intensive care unit monitoring in the immediate postoperative period, along with blood transfusions and stomach and bladder tubes. All of this imposes stress on the cardiovascular system. Also associated with this procedure are well recognized morbidity (15%) and mortality (2–7%) rates. See Ernst, C. B. "Abdominal Aortic Aneurysms," *New England J. Med.*, Vol. 328:1167–1172 (Apr. 22, 1993).

Today, there is the potential for a significantly less invasive clinical approach to aneurysm repair known as endovascular grafting. Parodi et al. provide one of the first clinical descriptions of this therapy. Parodi, J. C., et al., "Transfemoral Intraluminal Graft Implantation for Abdominal Aortic Aneurysms," 5 *Annals of Vascular Surgery* 491 (1991). Endovascular grafting involves the transluminal placement of a prosthetic arterial graft in the endoluminal position (within the lumen of the artery). By this method, the graft is attached to the internal surface of an arterial wall by means of attachment devices (expandable stents), one above the aneurysm and a second stent below the aneurysm.

Stents are devices that permit fixation of a graft to the internal surface of an arterial wall without sewing. Expansion of radially expandable stents is conventionally accomplished by dilating a balloon at the distal end of a balloon-catheter. In U.S. Pat. No. 4,776,337, Palmaz describes a balloon-expandable stent which has received the greatest experimental and clinical application for endovascular treatments. Also known are self expanding stents, such as described in U.S. Pat. No. 4,655,771 to Wallsten. These patents are hereby incorporated in their entireties, by reference.

Attachment of the stents above and below the aneurysm is a conceptually straightforward procedure when the aortic aneurysm is limited to the abdominal aorta and there are significant portions of normal tissue above and below the aneurysm (see FIG. 1). Unfortunately, 40–60% of aneurysms do not have suitable neck portions of normal tissue at the caudal portion (farthest from the head) of the aorta. Also, the severe tortuosity of the iliac arteries and the marked angulation of the aortoiliac junction compound the difficulty of fixing the stent in the caudal portion of the aorta. This situation is only exacerbated by the tendency of the abdominal aortic artery to elongate caudally during aneurysm formation. For want of sufficient normal aortic tissue to suitably attach a prosthetic graft at the caudal end of an aneurysm, or because of extension of the aneurysmal sac into the iliac arteries, bifurcated grafts have been developed that comprise a single body terminating with two limbs.

As a therapy to bypass an abdominal aortic aneurysm as well as any associated common iliac aneurysms, endoluminal deployment of a conventional bifurcated graft has presented significant issues to clinical operators in the field, primarily with respect to the positioning of one of the limbs of the graft in the contralateral iliac artery. The contralateral iliac artery is the artery that the conventional endoluminal bifurcated graft is not being advanced through. This procedure requires that both limbs of the graft be inserted into one branch of the femoral arterial system before being drawn or pulled over to the contralateral branch. This is to ensure that the graft is suitably positioned within the aorta and each of the right and left common iliac arteries. Even when tightly packaged, the bifurcated graft is a bulky device to advance through an often narrow single iliac artery.

The process of pulling or drawing one limb of the graft to the contralateral artery is time consuming and increases the risk of procedural complications, such as twisting and kinking of the graft-limb and injury to the vessel wall which can result in micro-embolization. As one limb of the graft is pulled across the frequently tortuous and twisted iliac artery anatomy, the graft may twist or kink. Any graft twist or kink may reduce or entirely cut-off blood flow to the arterial tree downstream thereof.

The procedure of drawing one limb of the prosthetic graft from one branch of the arterial system to the contralateral branch requires significant and skillful wire catheter manipulation within the aneurysmal cavity. See, for example, Chuter T. A. M., et al., "Transfemoral Endovascular Aortic Graft Placement," *J. of Vascular Surgery* 18:185–197, at 188–190 (August, 1993). This procedure may result in micro-embolization of clots which are known to form within aneurysmal sacs. If these clots are disturbed or dislodged from the aortic aneurysm, they may break up into small fragments and flow downstream to other arteries. The excessive wire manipulation may also induce "churning" within the aneurysmal cavity which can cause proximal reflux or retrograde flow of thrombotic or embolic material into the arteries that supply circulation to the kidneys, intestines and the liver.

Accordingly, there exists a need for a method for safely and effectively bypassing an aneurysm, such as an abdominal aortic aneurysm, located at or extending into a bifurcation in the vasculature, such as the common iliac arteries. There also exists a need for an attachment device that permits the collateral deployment of stents as mirror image pairs, as well as an apparatus for deploying such an attachment device.

SUMMARY OF THE INVENTION

These and other needs are addressed, according to one aspect of the invention, by a method of endoluminally bypassing blood flow through an aneurysm. The method comprises the steps of advancing a graftstent complex through each branch of the branched blood vessel, aligning the cephalic stents of each of the graftstent complexes relative to each other in a common vessel above the aneurysm, and deploying each of the aligned cephalic stents in the common vessel. When the aneurysm is in the aortic artery, the graftstent complexes are advanced through the femoral and iliac arterial system and the cephalic stents are aligned in a common region of normal aortic tissue above the aneurysm. The alignment step may further comprise rotationally orienting the stents so that an alignment surface on each stent engages the other stent when the stents are deployed. Of course, the method may be performed in passageways other than those that form the arterial system, and may be performed by advancing the graftstent complex from a common passageway to a branched passageway. When the inventive method is performed in the vascular system, the deployed vascular stents are preferably expanded in a non-circular configuration, for example, in a generally "D" shaped configuration, and may be expanded simultaneously. The deployed stents preferably hemostatically seal the graftstent complexes to the common vessel wall and to each other so that blood is excluded from the aneurysmal cavity.

The invention also provides an apparatus for rotationally aligning a pair of indwelling stents mounted on separate catheter shafts. The shafts rotatably support the indwelling stents. The apparatus includes an indicating means on a proximal portion of each of the shafts for indicating the relative rotational orientation of the stents. Rotation of the proximal portion of the shafts provides a corresponding rotation of the stents, so that the relative rotational orientation of the indwelling stents is indicated by the proximal indicating means. In one embodiment, the indicating means comprises a marker on the proximal end of each of the shafts.

The invention also provides an apparatus that radially expands a vascular stent into a non-circular configuration. The apparatus comprises a member which is movably mounted with respect to a catheter, a deployment wire connected to the member for axially moving the member with respect to the catheter, and a plurality of wings which partially surround the member to form a support surface for the stent. The apparatus expands the stent into a non-circular configuration through a connection of a plurality of first and second arms which are of different lengths. Each of the wings is pivotally connected to a rigid portion on the catheter by one of the first and second arms so that the wings connected to the first arms displace radially outwardly more than the wings connected to the second arms when the movable member is moved axially by the deployment wire. This apparatus may also be used for collaterally deploying a pair of stents within a common body lumen.

The invention also provides in combination with an expandable prosthesis an apparatus for deploying the expandable prosthesis with a non-circular cross-section at a site within a body lumen. The apparatus includes a support for supporting the expandable prosthesis while being delivered to the site within the body lumen, and a radially displaceable mechanical linkage connected to the support. The linkage expands the prosthesis to a non-circular cross-section when displaced radially outward and is adapted to deploy the expandable prosthesis when radially displaced. The linkage permits continuous fluid flow within the body lumen while the expandable prosthesis is being deployed.

According to another aspect of the present invention, there is provided an expanded vascular stent which has a non-circular cross-section. The vascular stent may be of the self-expanding variety, and preferably has a generally "D" shaped configuration. In the preferred embodiment, the "D" shaped stent has a curved edge and an alignment edge. The curved edge engages a body lumen when expanded, whereas the alignment edge engages a collaterally expanded vascular stent. A segment of graft material having at least one end cut on a bias is attached to the stent so that the graft material extends substantially between the proximal and distal ends of the stent along the alignment edge, yet only partially along the curved edge. This advantageously assists in hemostatically sealing the bypassed aneurysm from the patient's blood flow.

According to yet another aspect of the present invention, a graftstent complex for hemostatically bypassing an aneurysm is provided. The graftstent complex comprises a segment of graft material, a balloon-expandable stent, and a self-expanding stent. The segment of graft material is attached at one end to the balloon-expandable stent and at another end to the self-expanding stent. The graftstent complex may have the segment of graft material cut on a bias, as noted above.

These and other objects, features and advantages of the present invention will be readily apparent from the following detailed description of the invention taken in conjunction with the accompanying drawings.

BRIEF DESCRIPTION OF DRAWINGS

FIG. 1 is a diagrammatic view of a portion of a human vascular system depicting an abdominal aortic aneurysm which has been endoluminally bypassed in a manner previously described by Parodi et al.;

FIG. 1A is a diagrammatic view of a portion of a human vascular system depicting an abdominal aortic aneurysm and associated aneurysms of the left and right common iliac arteries;

FIG. 1B is the vasculature of FIG. 1A after exclusion of the aneurysm and attachment of a graft in conventional manner;

FIG. 1C is a cross-sectional view of FIG. 1A showing the placement of a bifurcated graft by a an endovascular technique previously described by Chuter et al.;

FIG. 4 is an enlarged view of a portion of FIG. 3 at yet a further stage of the method of the present invention wherein the caudal stent is deployed within the distal common iliac artery;

FIG. 6A is an enlarged detailed view of a portion of FIG. 2;

FIG. 7 is a side view of a deployment head useful with the present invention;

FIG. 8 is a longitudinal cross-section of the deployment head, taken essentially along line 8—8 of FIG. 5, and shown in a radially recoiled stance;

FIG. 9 is a cross-section taken along line 9—9 of FIG. 6 showing the long travel of two of the wings of the deployment head during deployment;

FIG. 10 is a cross-section taken along line 10—10 of FIG. 6 showing the short travel of the other two wings of the deployment head during deployment;

FIG. 18 is a cross-section taken along line 18—18 of FIG. 17 showing the catheter mounting subassembly in spaced proximity to the actuator subassembly;

FIG. 19 is a cross-section taken along line 19—19 of FIG. 17 showing the catheter mounting subassembly and the actuator subassembly in abutting relationship to one another;

DEFINITIONS

Figure 2:
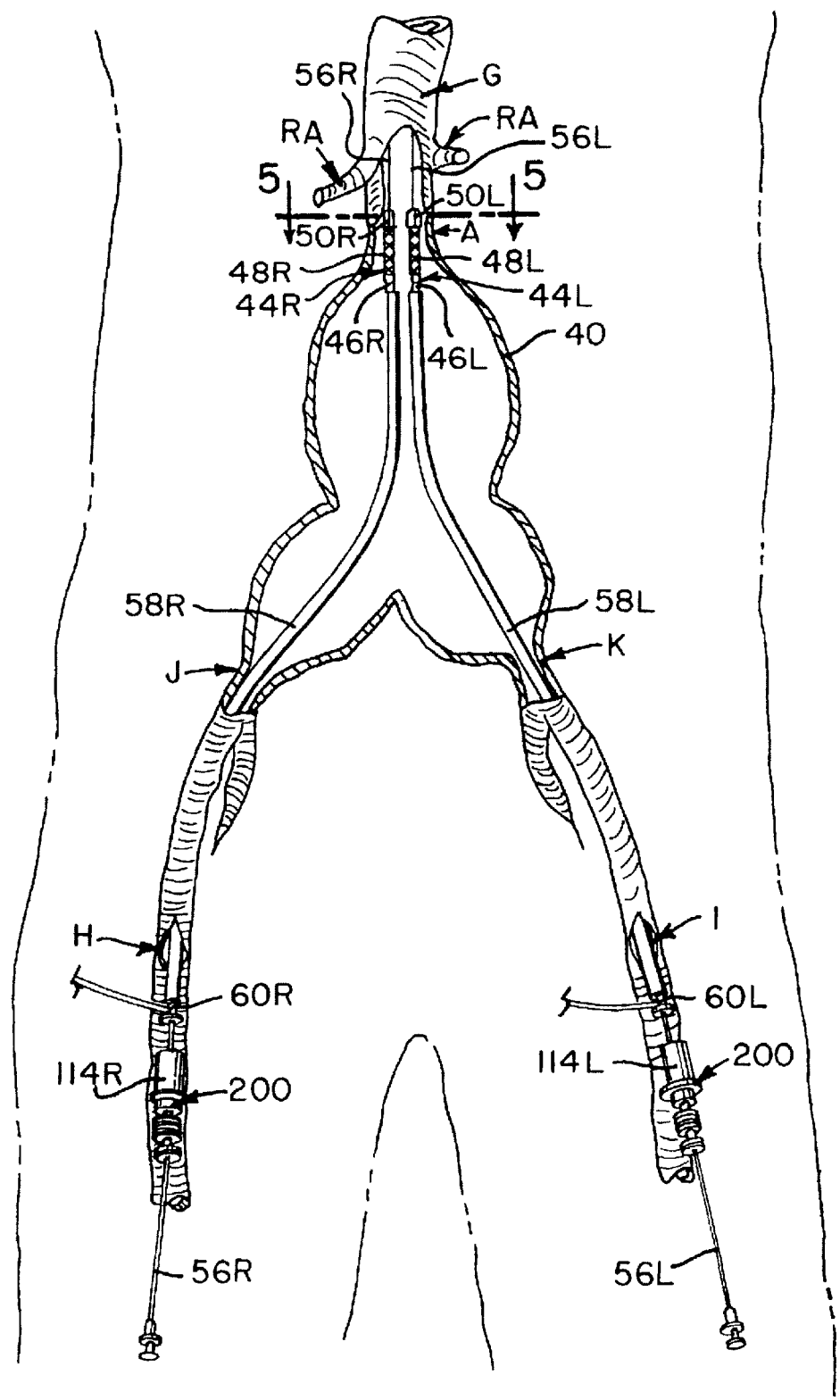
FIG. 2 is a cut-away view of the aneurysmal sac of FIG. 1A, shown in situ, with a deployment device advanced through each femoral artery in accordance with one stage of the method of the present invention.

The terms "distal" and "proximal" as used in this specification refer only to the catheter device itself and the stents being deployed, but not to the vasculature. The present method contemplates advancement of a catheter in a retrograde manner (against the flow of blood). Therefore, as the catheter is advanced distally from, for example, the femoral artery, it advances to a more proximal portion of the vasculature with respect to the heart, as understood by those skilled in the art. Thus, to avoid ambiguity, the vasculature is referred to with respect to the cephalic (closer to head) and caudal (further from head) directions. Also, as used in this description and in the claims, the term "above", in the context of relative positioning with respect to the aneurysm, refers to the region cephalic of the aneurysm, for example, within the aorta, whereas "below" refers to the region of the vasculature caudal of the aneurysm, for example, within the common iliac arteries.

DETAILED DESCRIPTION OF THE INVENTION

The present invention provides a method and apparatus for treating aortic aneurysms which extend to the aortoiliac junction without a suitable region at the junction of the aorta and the iliac arteries for seating a stent or other attachment device. By seating, it is meant that the graft is implanted, fixed or otherwise attached to the vasculature. By way of overview and introduction, the present inventive method and apparatus provide separate grafts to the aorta through each branch of the iliac arterial system. These grafts are unified upon deployment to form a new, double barrel, bifurcated graft in the vicinity of the renal arteries.

Conventional procedures are discussed first to provide a better appreciation for the clinical situations that would benefit from the use of the method and apparatus of the present invention.

A. Prior Art Techniques

In FIG. 1 there is a diagram of a vascular system that depicts, in part, the arterial system in the vicinity of the abdominal aorta. In order to use a tubular endoluminal graft, a sufficient length of normal artery both above and below an aortic aneurysm 40 is required so that a graftstent complex 44 can be effectively seated or attached. The graftstent complex 44 comprises a thin-walled, crimped, knitted graft 46 of polyester, expandable polytetrafluoroethelyne (ePTFE), or similar material that overlaps and is sutured to at least a cephalic stent 48. As shown in the Figures, the graftstent complex 44 further includes a caudal stent 49, but the invention has application with a graftstent complex 44 having only one stent, e.g., the stent 48. Suitable vascular grafts that may be used include Model 80S07TW by Impra, of Tempe, Ariz.; and Model VT06070L by Gortex, of Flagstaff, Ariz. One stent usable with the invention is the stent described in U.S. application Ser. No. 08/278,546 of Marin et al., filed on Jul. 19, 1994, for INTRALUMINAL STENT, the entirety of which is incorporated herein by reference.

As is depicted in FIG. 1, a stent 48 anchors the tubular endoluminal graft above the aneurysm at point A and another stent 49 below the aneurysm at point B. When the length of the neck is insufficient to seat a stent at point B, a bifurcated device is necessary. The anatomic arrangement that would benefit from a bifurcated device is depicted in FIG. 1A. Here, there is insufficient normal artery to seat the stent 49 at point C because of the aneurysms in the associated common iliac arteries.

When the anatomic constraint of FIG. 1A is present, the standard vascular surgical approach requires that a bifurcated extraluminal graft procedure be performed. This procedure is performed by making a large abdominal incision from the breast-bone down to the pubic bone in the middle of the abdominal wall (not shown). The intestines are pushed aside and the aneurysm is approached directly where it sits adjacent to the spine, near the patient's back. With clamps placed above the aneurysm at point A and additional clamps placed on the iliac arteries at points D and E, blood flow is controlled so that an artificial graft 42 can be sewn into position as a new conduit to replace the diseased aorta 40, as shown in FIG. 1B. This procedure involves an extensive operation and recovery period, with an intensive care unit stay and a significant period of post procedure convalescence.

It is difficult to safely endoluminally deploy a conventional bifurcated graft when the anatomic constraint of FIG. 1A is present. Because both limbs are inserted and advanced through a single branch of the femoral arterial system, one of the limbs must ultimately be pulled or drawn into the contralateral or opposite branch so that the graft is suitably positioned across both the aortic aneurysm and the associated common iliac aneurysms to supply circulation to each of the lower limbs. Importantly, bifurcated grafts are frequently too bulky to advance through a single iliac artery, especially in view of the fact that the graft-limb for the contralateral branch must be inserted together with the graft-limb of the ipsilateral branch. In addition, care must be taken to not twist or kink the graft as it is placed in the contralateral artery. The caudal portion of the graft must not stretch across the mouth of the internal iliac artery which would result in inadvertent occlusion of that artery (see point F). The procedure of drawing one limb of the prosthetic graft from one femoral artery to the contralateral femoral artery requires placement of a cross-femoral catheter 41 using a closable wire basket 43 prior to graft insertion (as shown in FIG. 1C). This procedure requires significant and skillful wire catheter manipulation, frequently within the aneurysmal cavity. Meanwhile, care must be taken to avoid disturbing or dislodging thrombic or embolic material from within the aneurysmal sac. Additional factors such as the severe tortuosity of the iliac arteries and the marked angulation of the aortoiliac junction resulting from the tendency of the abdominal aortic artery to extend caudally during aneurysm formation combine to make deployment of endoluminal bifurcated grafts time consuming and at increased risk of procedural complications and failure.

B. Method and Apparatus of the Present Invention

FIG. 2 depicts the aneurysm 40 in the infrarenal aorta and the common iliac arteries. The infrarenal aorta is that portion of the aorta disposed caudal of the left and right renal arteries RA. It has been empirically observed that as much as eighty percent of all abdominal aortic aneurysms occur in the infrarenal aorta. Because the aneurysm extends through the aortoiliac junction, no normal aortic arterial tissue at the caudal end of the aorta is present to which a caudal stent may be secured. Conventional vascular surgical therapies for this anatomical arrangement have been noted above, along with the difficulties posed to operators performing endoluminal bypass procedures using conventional bifurcated grafts.

As shown in FIG. 2, the infrarenal aorta extends caudally to the common iliac arteries which branch left and right. In the Figures, elements introduced through the left branch of the patient's vasculature (the right side of FIGS. 2 and 3) have an "L" designation after their respective reference numerals and elements in the right branch have an "R" designation, and such elements are more generally referred to throughout this specification without such branch designations when there exists bilateral symmetry. Each common iliac artery further branches into the internal and external iliac arteries. The external iliac artery becomes the femoral artery below the inguinal ligament (not shown). In conventional manner, the femoral artery is entered within the thigh by an arterial incision where the vessel is close to the undersurface of the skin. A guide catheter is then introduced into the patient's vasculature.

A guidewire 56 may now be endoluminally snaked through the guide catheter and beyond to a position G in the patient's thoracic aorta, above the aneurysm 40. One suitable introducer catheter that may be used as the guide catheter is disclosed in U.S. application Ser. No. 08/243,190 of Marin et al., filed May 13, 1994, for DEVICE FOR DELIVERING AND DEPLOYING INTRALUMINAL DEVICES, the entirety of which is incorporated herein by reference. In particular, a conventional angiographic guidewire 56L,R is inserted into each groin through incision points H and I, as shown in FIG. 2. These incisions expose the common femoral arteries on the right and left sides. The guidewires are separately advanced until their distal ends are well above the aneurysm within the vasculature (point G). The guide wire 56 is at least 0.025 inches in diameter, and preferably 0.035 inches or more. The guide wire may be of tempered stainless steel and is conventionally covered with a synthetic material, such as TEFLON. The guidewire may remain in a fixed position throughout the endoluminal bypass procedure.

After the guidewires 56R and 56L are in place, guidesheaths 58R and 58L are introduced through the incisions H and I in a conventional fashion until their distal ends are positioned just below the point of attachment for the cephalic stents. These guidesheaths 58L,R function in conventional fashion to assist in positioning the deployment catheter within the patient's vasculature.

In accordance with the invention, instead of using a single bifurcated graftstent complex, two individual graftstent complexes 44L,R are introduced separately through the guidesheaths 58L,R and deployed in such a way that the cephalic stents 48 are joined together to in effect form a bifurcated graft in situ. This is accomplished by loading individual graftstent complexes 44L,R on separate deployment catheter shafts 60L,R and introducing the catheters through incisions H and I, respectively, into the guidesheaths 58L,R. Thus, with reference to FIG. 2, each of the graftstent complexes will be long enough to extend from attachment point A to attachment point J or K. In accordance with the presently preferred embodiment, each cephalic stent 48L,R is positioned on a mechanically expanding deployment head 50, as described below, but may also be deployed on a preshaped balloon 61, for example, a balloon that expands in a non-circular configuration, and preferably a generally "D" shaped configuration.

The deployment-catheters 60L,R with the graftstent complexes 44L,R mounted thereon are advanced through the guidesheaths 58L,R, and the cephalic stents 48 are positioned adjacent each other at the desired point of attachment A. As described below, at that point, the two adjacent stents 48 are simultaneously deployed, in effect, forming a "double-D" configuration with the two cephalic stents 48 adhered to each other along a common surface and secured to the aorta at their outer circumference.

After the cephalic stents 48 have been deployed, the caudal stents 49L,R (FIG. 3) are positioned at the attachment points J and K. The caudal stents 49L,R are preferably of the self-expanding type so that when the guidesheaths 58L,R are withdrawn, the caudal stents 49 expand automatically to attach themselves at points J and K.

Figure 3:
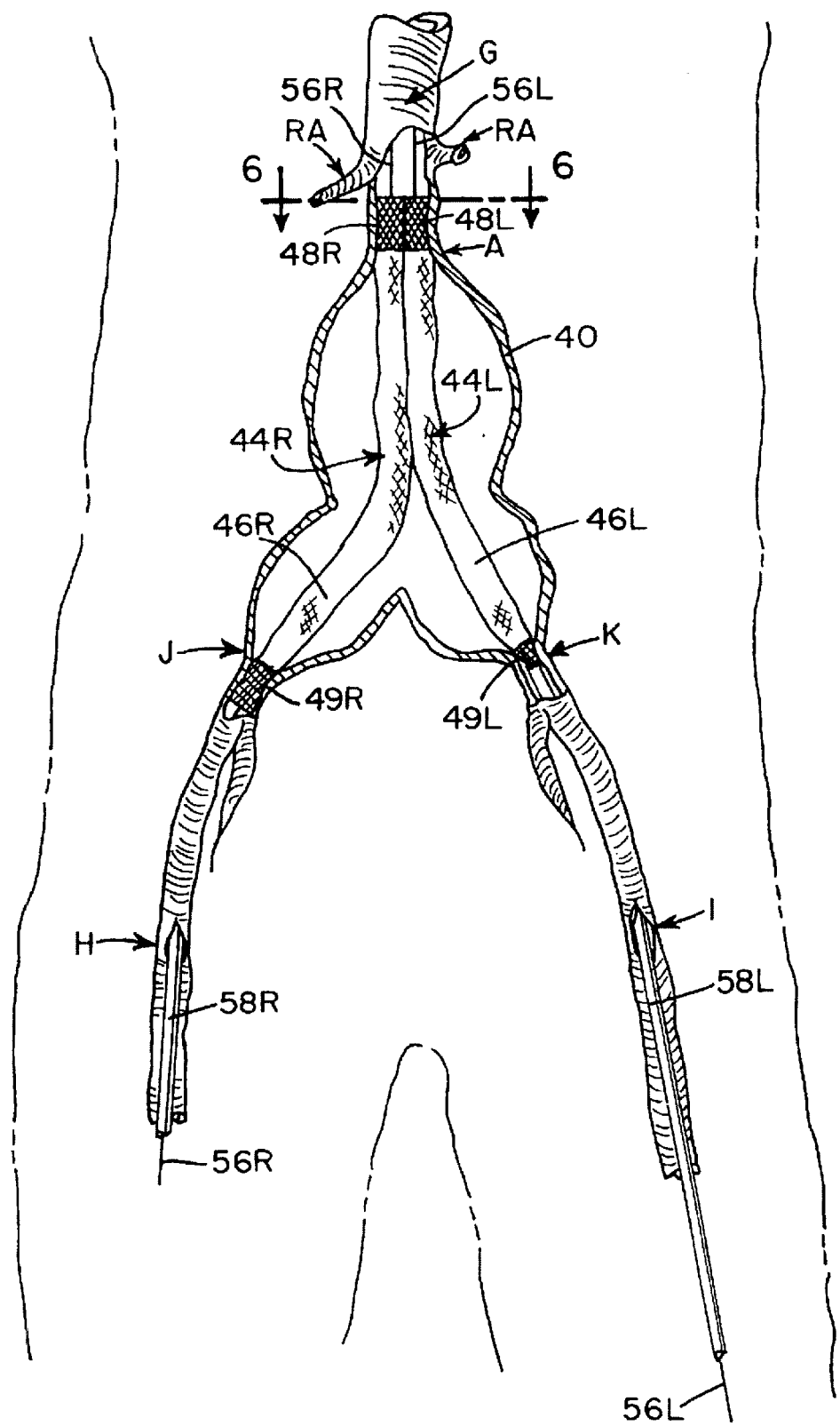
FIG. 3 is the same view as FIG. 2 at a further stage of the method of the present invention wherein the cephalic stents have been deployed, and the right caudal stent (left side of figure) is in the deployed position.

The result, as shown in FIG. 3, is that the aneurysm 40 is bypassed by the graftstent complexes 44L,R, which are hemostatically joined together by the cephalic stents 48 and are separately secured in each iliac arterial branch by the caudal stents 49L,R.

As indicated above, in the preferred embodiment of the invention, the cephalic stents 48L,R are deployed by a mechanical device similar to the device shown in U.S. patent application Ser. No. 08/196,278 for APPARATUS AND METHOD FOR DEPLOYMENT OF RADIALLY EXPANDABLE STENTS BY A MECHANICAL LINKAGE, filed Feb. 10, 1994, but modified to deploy the individual vascular stents in a manner such that when expanded, they are non-circular in cross-section, and preferably generally "D" shaped in cross section. Such a deployment device is described in detail below with reference to FIGS. 4–22.

With fluoroscopic assistance, the site for placing the cephalic stent 48 is defined, typically in the vicinity of point A, somewhat below point G, as shown in FIG. 2. In each of the Figures, the cephalic stent corresponds to the stent located more distal from the respective point of incision than the caudal stent. An angiogram is also used to define the points for fixation of the caudal portion of each limb of the bifurcated graft, for example, in the vicinity of points J and K.

The graftstent complex 44R of a suitable predetermined length to bypass the aortic aneurysm and the right iliac artery aneurysm, may be mounted on a deployment head 50R of a flexible catheter 60R and covered with the guidesheath 58R. Similarly, a graftstent complex 44L which may be of a different length than the graftstent complex 44R is mounted on a separate deployment head 50L and covered with a guidesheath 58L for deployment in the left arterial branch. The lengths of each graft 46L,R is determined in accordance with pre-procedural angiogram and computerized axial tomogram (CT scan) data, or otherwise.

Once the necessary lengths of the grafts 46L,R are known, suitable graftstent complexes 44L,R may be loaded onto the deployment catheters 60L,R for separate advancement to the site of the aneurysm. Each catheter shaft 60 includes the deployment head 50 at its distal end (see FIG. 7). Each deployment catheter 60L,R is separately advanced over the proximal end of a respective guidewire 56L,R and passed through the groin incision for advancement to point A, above the aneurysm. A fluoroscopic image of the patient's abdominal cavity may assist locating the heads 50L,R relative to the designated site. Where heads 50L,R are formed of plastic or epoxy materials, they are advantageously provided with radiopaque portions to assist in the fluoroscopic alignment process. The guidesheaths 58L,R are placed over each prosthesis for smooth delivery to the site of the aneurysm 40. Once the heads 50L,R have been advanced to a point above the aneurysm, the guidesheaths 58L,R are pulled back by a sheath retractor (not shown) to expose the cephalic stents 48L,R (FIG. 2). Each of the guidesheaths 58L,R is withdrawn prior to displacement of the wings. Thus, a graft which is smaller than permissible by conventional bifurcated graft designs transits through each iliac artery to the aorta to achieve isolated or separate reconstruction of each iliac artery. The reduced overall graft profile affords the operator a safer and smoother path through the tortuous arterial system.

Because each graftstent complex 44 transits each iliac artery independently, there is no need for transfemoral crossover wires or catheter manipulations to draw one of the grafts 46L or 46R to the opposite side. This is distinctly different than other endoluminal bifurcated procedures, such as described above. As a result, the present invention affords reduced operative time and a safer simplified procedure.

Once each head 50L,R has been advanced to the designated site, a catheter mounting subassembly 200 located at the proximal end of each of the shafts 60L,R, is joined with a respective actuator subassembly to form assembled control mechanisms 54 (see FIGS. 18 and 19). These subassemblies are to ensure that the distention of the wings 52 is certain and precise, and are described below.

Figure 5:
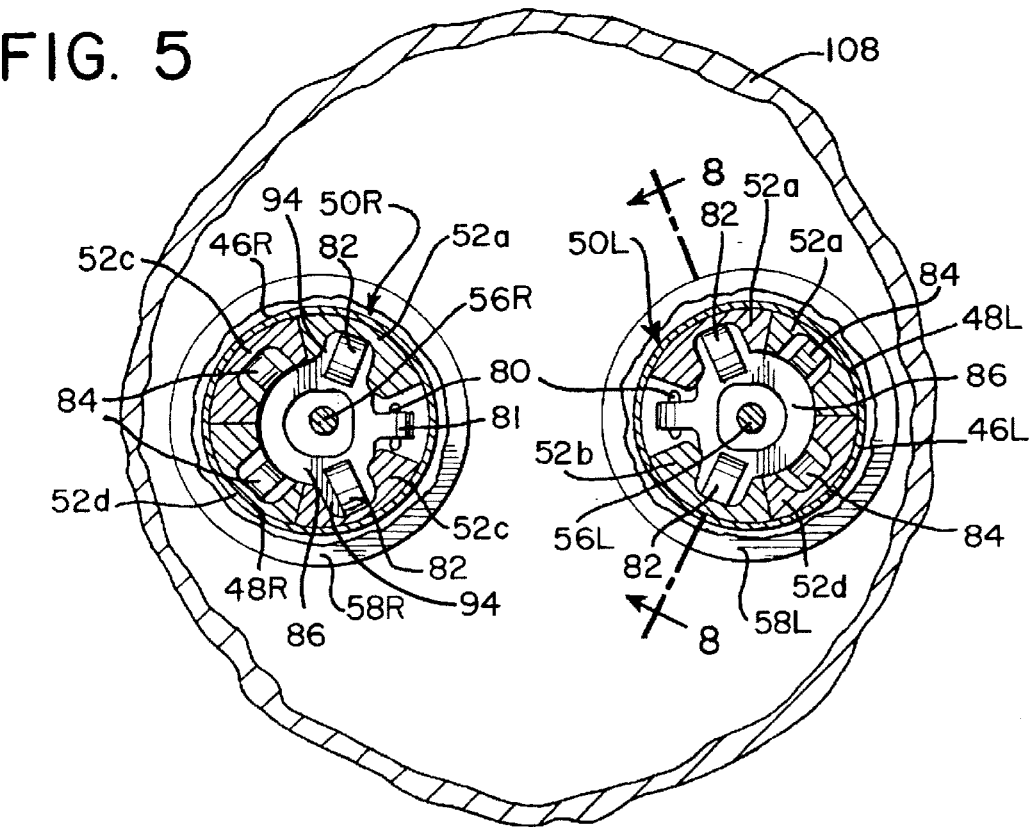
FIG. 5 is a cross-section taken along line 5—5 of FIG. 2 showing the deployment devices contained within delivery sheaths, as they may be used with the present inventive method, surrounded by normal aortic tissue prior to deployment of the cephalic stent.

The cephalic stents 48L,R must be collaterally and rotationally aligned prior to their deployment. Collateral alignment is best determined by fluoroscopy or by intraluminal ultrasound. This involves positioning the cephalic stents 48L,R in parallel within the vasculature relative to the head. Rotational alignment can be determined by fluoroscopy or by alignment markers located on, for example, the graft material 46L,R or a proximal portion of each of the catheters 60L,R, external to the patient. Alternatively, the stents 48L,R may include a thickened portion as a marker. Other ways of providing markers are known to those skilled in the art. As discussed in further detail below, the heads 50L,R are connected to the distal end of the catheter shafts 60L,R. The catheter shafts 60L,R are rotatably supported at their proximal ends by the nose cones 114L,R of the control mechanisms 54L,R. Rotation of the respective nose cones 114L,R provides one-to-one corresponding rotation at the corresponding deployment head 50L,R. Thus, an operator can rotationally align the separately advanced stents by means of markings on the proximal end of the shafts 60L,R, external to the patient. FIG. 2 shows the stents 48L,R collaterally aligned. FIG. 5 shows the same stents 48L,R rotationally aligned.

Once aligned, the stents 48L,R are preferably simultaneously expanded by an actuator or control mechanism 54. An actuator and deployment device used with the present invention is illustrated in the Figures and described below. A similar apparatus for expanding stents is generally described in co-pending U.S. application Ser. No. 08/196,278 filed Feb. 10, 1994, the entire application being incorporated herein by reference. The actuator causes each of the deployment heads 50L,R to expand cephalic stents 48L,R beyond the elastic limit of the stent material, as shown in FIG. 3. The actuator can apply a force sufficient to restore a stenosed artery to its original, unstenosed diameter by flattening plaque or other embolic material. Each of the expanded stents 48L,R creates a friction seal against the aortic wall and against the adjacent aligned stent.

A significant feature of the deployment device as may be used with the present invention is that it expands stents into a non-circular, and preferably generally "D" shaped configuration. When rotationally aligned, as shown in FIGS. 5 (undeployed) and 6 (deployed), the pair of simultaneously expanded "D" shaped stents or cephalic stents 48 have their alignment edge portions, which may be generally straight, back-to-back frictionally engage one another whereas the curved edge component of the "D" shaped stents directly engage the underlying arterial wall to seal the grafts in position. The collaterally and rotationally aligned stents therefore form a bifurcated circular or oval configuration within the abdominal artery.

It is preferred that the graft material 46 extend along the entire alignment edge of the "D" stent while only extending partially along the curved segment, as best seen in FIG. 6A. FIG. 6A shows the graft material 46L,R of each of the graftstent complexes 44L,R cut on a bias. The stents 48L,R are preferably rotationally aligned so that the graft material extending along the entire margin of the stent 48L faces the graft material extending along the entire margin of the stent 48R. Once deployed, the cloth-to-cloth union of the graft materials 46L,R is believed to be more likely to clot and seal the graftstent complexes 44L,R to one another, to the exclusion of the aneurysmal cavity 40 so as to prevent blood from flowing into the aneurysmal sac 40. In this manner, a hemostatic seal may be achieved between the cephalic stents 48L,R, once the stents have been deployed.

Of course, the "D" stent need not have a straight edge. Other configurations would provide a significant surface for frictional engagement with the adjacent expanded stent, for example, sinusoidal, triangular, trapezoidal abutting edges.

The individual "D" shaped stented grafts are preferably attached to one another and the body vessel by barbs which remain within the surface of the stent when the stent is in its unexpanded condition, but which extend from the surface of the stent when the stent is expanded. A suitable stent for this application is described in U.S. application Ser. No. unassigned of Marin et al., filed on Jul. 19, 1994, for INTRALUMINAL STENT. As the stent is deployed, the barbs are also deployed so that when the stent contacts the surface of the blood vessel the barbs penetrate the inner lining of the blood vessel to anchor the stent in place. At the same time, the barbs penetrate an adjacent graftstent complex 44L or 44R. This unifies the two individual prosthetic grafts as a single bifurcated graft sufficient to form a fluid tight seal therebetween and against the arterial wall. This stent design advantageously permits both a friction seal anchor at the time of deployment and provides a sharp puncture attachment into the arterial wall and into the graft material of the aligned adjacent stent. This provides adequate anchoring for both grafts to each other as well as each graft to the arterial wall. When graft material is provided along the entire margin of the expanded stent which abuts the other stent, one stent's barbs engage the covering graft material rather than the metal of the adjacent stent. This should provide a fluid tight seal between the two endoluminal grafts.

Once both of the endoluminal grafts 44L,R have been fly fixed to each other and into the arterial wall above the aneurysm, the caudal end of each limb of the cephalically unified graft may be attached separately within each branch of the iliac arterial system. Fixation is preferably accomplished by means of self-expanding mesh-like stents, such as described in U.S. Pat. No. 4,665,71 to Wallsten, but the invention is not so limited. Stents 49 may be the same type as stents 48, or some other type known in the art. When loaded inside the guidesheath 58, such stents exhibit a small, collapsed profile that is substantially equivalent to the inside diameter of the containing guidesheath. However, when the guidesheath 58 is withdrawn, the caudal stent self-expands in a spring-like manner to a relatively larger tubular structure. At point L in FIG. 3, the guidesheath 58 is shown partially withdrawn from the stent 49 in the left branch of the iliac artery, below the aneurysmal part of the vessel. The upper portion of the stent is illustrated as having a conical shape, the uppermost margin being fully expanded and its lower portions still being contained within the guidesheath 58 with a compressed profile. Referring now to point M in the right arterial branch for comparison, the stent has assumed its naturally larger, expanded configuration because the guidesheath 58R has been entirely withdrawn from the stent 49. This stent bears against normal tissue in the common iliac artery at J. Although not shown in the left branch, further withdrawal of the guidesheath 58L beyond point L will permit the stent in the left branch to fully expand and fix the lower limb of the graft within the patient's vasculature.

Once each of the self-expanding stents 49L,R has been released, an arteriogram is performed to ensure that the grafts 46 are appropriately anchored to the arterial wall and that the aneurysm 40 is excluded from the circulation. A successfully deployed graftstent complex 44 will not permit blood to enter into the aneurismal sac 40. At the completion of the procedure, the catheters, introducers and guidewires are removed and the incisions in the right and left femoral arteries are sutured by standard vascular surgical anastomosis techniques. The skin is then closed with standard skin closure procedures. It is anticipated that with miniaturization, this procedure could be performed by a percutaneous puncture of the artery.

The mechanism of a preferred embodiment of the deployment head 50 is now explained with reference to FIGS. 4 through 13.

FIG. 5 shows a cross-sectional view of a body lumen 108 with the catheters 60L,R disposed therein. Each catheter 60 terminates distally with the deployment head 50. As illustrated, one of the deployment heads 50L,R is rotated 180° with respect to the other, however, the deployment heads are otherwise identical. One of the deployment heads 50L,R has been advanced through the body lumen 108 over the guidewire 56R whereas the other has been advanced over the guidewire 56L. The cephalic stent 48 is mounted on the deployment head 50 which has a support surface comprised of four radially displaceable wings 52a, 52b, 52c, and 52d (see FIGS. 5 through 10). All of the wings may be dimensionally the same. A graft material 46 is sewn at least to the cephalic stent 48 and preferably to the caudal stent 49 to form the graftstent complex 44. The deployment head, stent and graft are recessed within the guidesheath 58 to facilitate noninjurious advancement and withdrawal of the catheter through the patient's vasculature. The guidesheath is withdrawn relative to the deployment head, as noted above, prior to deployment of the stents 48L,R.

Figure 6:
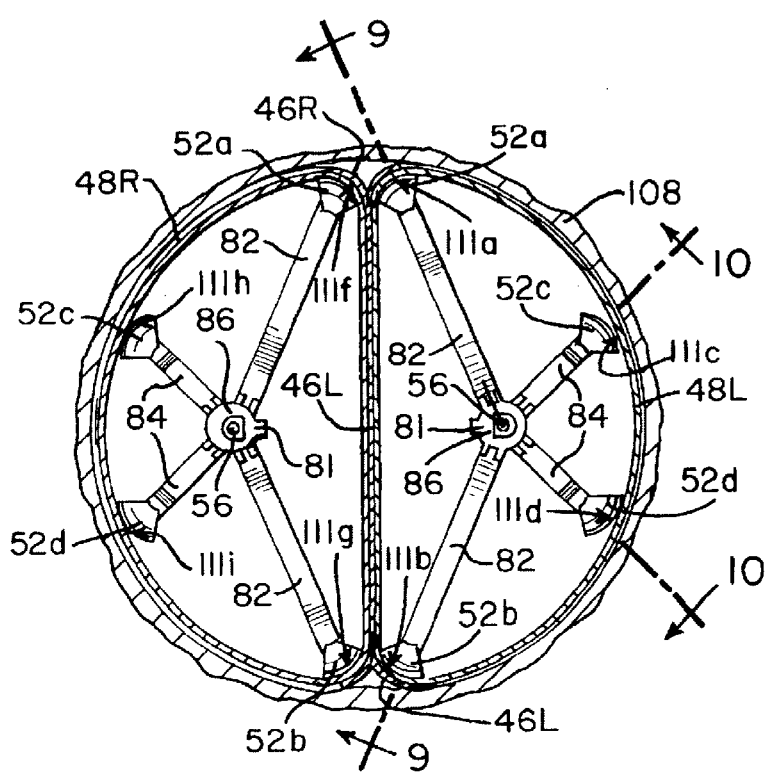
FIG. 6 is a cross-section taken along line 6—6 of FIG. 3 showing the same deployment devices after deployment of the cephalic stent.
Figure 11:
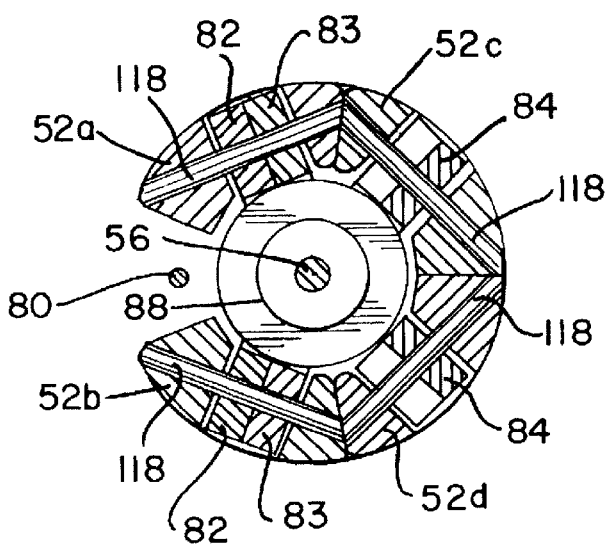
FIG. 11 is a cross-section taken along line 11—11 of FIG. 8.

The stents 48 may have an unexpanded diameter of three to five millimeters or less for delivery purposes. At the desired location, the stent on the head 50 is radially distended to an expanded diameter by a mechanical linkage actuated by the control mechanism 54, described below. The radial expansion of the stent is continued until at least a part of it invaginates into an arterial wall and fastens itself by a friction seal, as shown in FIG. 6. The wings may also be expanded so as to compress any deposits on the arterial wall which constrict the natural, unoccluded arterial diameter. As best seen in this Figure, the wings 52a,b are further radially displaced within the body lumen than the wings 52c,d.

In FIG. 7, there is seen a longitudinal view of the head 50 which includes an annular support 59 press fit onto the distal end of an elongate flexible shaft 60. The shaft 60 comprises a wire wound coil 66 surrounding a multilumen plastic catheter 68 (not shown). The catheter 68 permits axial movement of several control wires which extend into the head 50 (see FIG. 13) and into the control mechanism 54 (see FIG. 18), as described below. The catheter 68 also has a central lumen 70 that receives the proximal end of the guide wire just before the head 50 is advanced into the patient's vasculature. The proximal end of shaft 60 is retained with the nose cone 114.

The apparatus of the present invention deploys the stents 48 by radially displacing the wings 52 through a mechanical coupling that consists of a pair of arms 82,83 associated with each of the wings 52a,b (shown in FIG. 8) and a mechanical coupling of the arms 84 associated with each of the wings 52c,d (shown in FIG. 10), together with a tubular slide 86 and an initiator 88. The tubular slide and the initiator are axially slideably mounted with respect to the guide wire. In addition, the tubular slide 86 is connected to the wings 52a,b by the arms 82 and the initiator 88 is commonly associated with each of the wings 52a,b,c,d. The distal ends of the arms 82 are pivotally attached to the distal end of the slide 86 by pins 96 through bifurcated lugs 94. A deployment wire 80 (see FIGS. 11–13) extends from the control mechanism 54 through the shaft 60 and, at its distal end, is tied to or looped through a hole in a lug 81 at the distal end of the slide 86 (see FIG. 5). The proximal ends of the arms 82 are pivotally attached to the distal ends of the arms 83 and an intermediate part of a corresponding wing 52a,b, by pins 118 (see FIGS. 9–11). The proximal ends of the arms 83,84 are pivotally mounted to the annular support 59 by pins 120, as best seen in the cross-sectional view of FIG. 13. Hence, tension applied to the looped deployment wire 80 will cause the arms to buckle (FIGS. 9–10) which in turn deploys the wings 52a,b,c,d outwardly. The deployment wire 80 is anchored at its proximal ends, preferably, to a multiply ribbed anchor 90 (FIG. 17) that mates with the control mechanism 54 such that a calibrated force may be directly transmitted from the control mechanism 54 to the tubular slide by squeezing a trigger 92 to effect a radial displacement of the wings 52a,b, all while intraluminal fluid flow in the region of device deployment is minimally impeded within the patient's vascular system. The deployment wire 80 is capable of transmitting compressive forces, and preferably has a diameter of 0.014 inches or less. Thus, when the trigger 92 is released, the deployment wire moves axially toward the distal end of the head 50 thereby towing the tubular slide to its rest position and radially recoiling the wings 52a,b.

In contrast to balloon based devices, therefore, the direct transmission of a physical force from the trigger 92 to the head 50 causes the device of the present invention to operate substantially instantaneously without the delays associated with the filling of a balloon. The mechanical device is readily adapted (as shown in the Figures) to expand a stent in a "D" shaped configuration. Notwithstanding the perceived advantages of using the deployment head 50 shown in FIGS. 4–13, the invention may be deployed by a balloon angioplasty catheter having an inflatable balloon portion that is preshaped to collaterally deploy a pair of stents 48L,R. Preferably, the inflatable balloon 61 portion is preshaped in a generally "D" shaped configuration. The actual means used to deploy the collateral stents, however, is not critical to the inventive method.

A slot 98 (FIG. 7) in each of the wings 52 accommodates the lugs 81,94 and the coupling arms 82 when the wings 52a,b,c,d are recoiled. This allows for a more compact profile of the head 50 for intraluminal delivery and removal after the surgical procedure is complete. The head 50 can be formed with a profile of approximately five millimeters.

The head 50 includes the cylindrical initiator 88 for initiating the radial motion of the wings from their recoiled configuration, as shown in FIG. 8. This makes it easier to fully deploy the wings 52a,b, when tension is applied to the deployment wire 80. An initiator wire 20 78, which extends through the central lumen of the initiator 88, is anchored to the initiator in a circumferential slot 100, and is used to axially slide the initiator with respect to the arms 83,84 (see FIG. 12). The slot 100 is preferably formed with a pair of opposing holes 102 through which the initiator wire 78 may be threaded and wrapped securely. A force applied to the proximal end of the initiator wire 78 by the control mechanism 54 slides the initiator 88 with respect to the guide wire 56. Advancement of the initiator 88 toward the distal face of the annular support 59 causes it to engage sloped surfaces 104 of the arms 84 and sloped surfaces 103 of the arms 83. Preferably, the sloped surfaces 103,104 have a 15° pitch. Continued proximal movement of the initiator 88 causes it to bear against the sloped surface of each arm 83,84. In response to this pressure, each coupling arm 82,83,84 buckles slightly, i.e., the distal portions of the coupling arms pivot slightly away from the tubular slide 86 to initiate movement of each respectively coupled wing slightly radially outward, as perhaps best seen in FIG. 4 The coupling arms 82 of the wings 52a,b similarly pivot about the lugs 94 while the tubular slide 86 is moved slightly toward the distal face of the annular support 59. Advantageously, the portion of the initiator 88 that bears against the surfaces 103,104 is shaped as a frustrum so that frictional forces are minimized. Reduced frictional forces permit use of a thinner, more compact initiator wire 78. Preferably, the initiator wire is 0.014 inches or less in diameter.

For certain types of stent or attachment devices where low radial forces are required, only one deployment means may be required.

After the initiator 88 has caused the arms 82,83,84 to buckle slightly and the slide 86 has started to move, the wings 52a,b can be fully radially displaced, as shown in FIG. 9, by advancing the tubular slide 86 toward the distal face of the annular support 59 by squeezing the trigger 92 to apply tension to the deployment wire 80. FIG. 6 shows the head 50 fully radially displaced within a body lumen 108. Here, the tubular slide 86 has been retracted toward the distal face of the annular support 59, as by the trigger 92, to bow the coupling arms 82,83,84 outward and radially separate the wings. As the stent support surface separates with the radial motion of the wings, the stent deforms at four contact points 111a, 111b, 111c, and 111d into a "D" shaped configuration. The stent is anchored to the walls of the body lumen when the wings 52a,b have dilated substantially to the diameter of the body lumen. Thus, if the body lumen 108 were the abdominal aortic artery, the wings 52a,b would be dilated to approximately 35 to 40 mm. Because two stents are collaterally expanded, a mirror image of contact points 111f, g, h, and i, are formed when the stents are suitably aligned. As a result, a double barrel "D" shaped circularly configured bifurcated graft forms a new aortic bifurcation in the vicinity of the renal arteries extending to the region of the internal iliac arteries (FIGS. 3 and 6).

Figure 12:
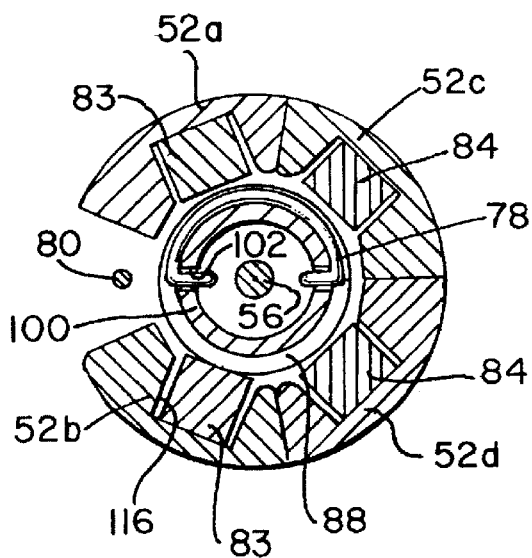
FIG. 12 is a cross-section taken along line 12—12 of FIG. 8.
Figure 13:
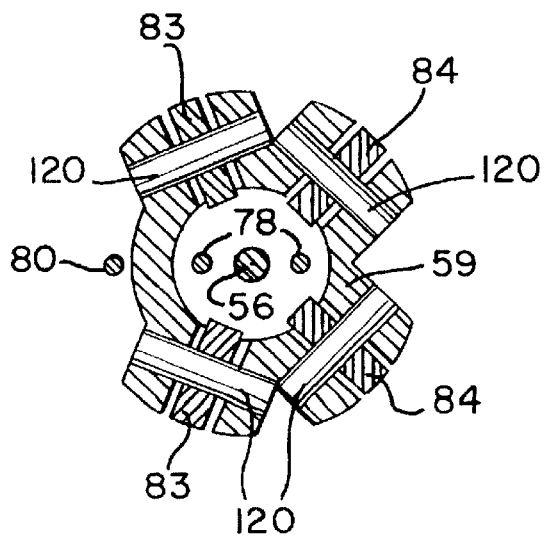
FIG. 13 is a cross-section taken along line 13—13 of FIG. 8.

Each of the wings preferably has a stepped inner surface 116 to accommodate the coupling arms 82,83,84 (see FIG. 12). Each wing also has a primary rib 122 at a distal end and a secondary rib 124 at a proximal end. A recess 126 between the wings holds the stent in place (see FIGS. 7 and 9).

Advantageously, the head 50 and the shaft 60 form a delivery system that can be preconfigured with a particular graftstent complex 44 of suitable length for the procedure. However, because placement of the caudal stent 49 is adjusted in accordance with the particular anatomical requirements of the outflow artery, less rigorous length requirements are imposed for the selection of graft material prior to surgery. This may permit a reduced selection of graftstent complex lengths to choose between when selecting the graftstent complexes 44 for each branch of the iliac system.

The maximum extent of expansion of the "D" stent, which occurs along the line described by the wings 52a, b (which wings separate radially at an obtuse angle, preferably 134°), is directly controlled by the travel of the trigger 92 which governs the tubular slide 86. This travel can be calibrated to a predetermined level of expansion, e.g., thirty-five mm. Once expanded to the predetermined size, after re-evaluation of the prosthesis positioning, the stent can be immediately redilatated to a larger size without the introduction of a new deployment head 50 or a catheter exchange. The linkage and wings are sufficiently rigid to dilate the stent, or a stenosis to the predetermined size regardless of the presence of plaque and the like. The stent can be incrementally dilated to larger sizes on a moment-by-moment basis depending on real time fluoroscopic images and the operator's discretion as a function of the actual arterial dimensions instead of relying on estimated dimensions that are conventionally made prior to the procedure using arteriography and CT scanning. This affords a decrease in blood loss during such redilation procedures and cuts down on the amount of time and cost involved with procedures which could potentially require multiple angioplasty catheter exchanges to appropriately dilate the stent. It also reduces the risk of graftstent migration which could occur during such balloon catheter exchanges.

In FIGS. 15–22, there is seen the control mechanism 54 as may be used with the deployment devices inserted into each femoral artery. Several views are given so that the geometry of the control mechanism 54 can be better appreciated.

Figure 15:
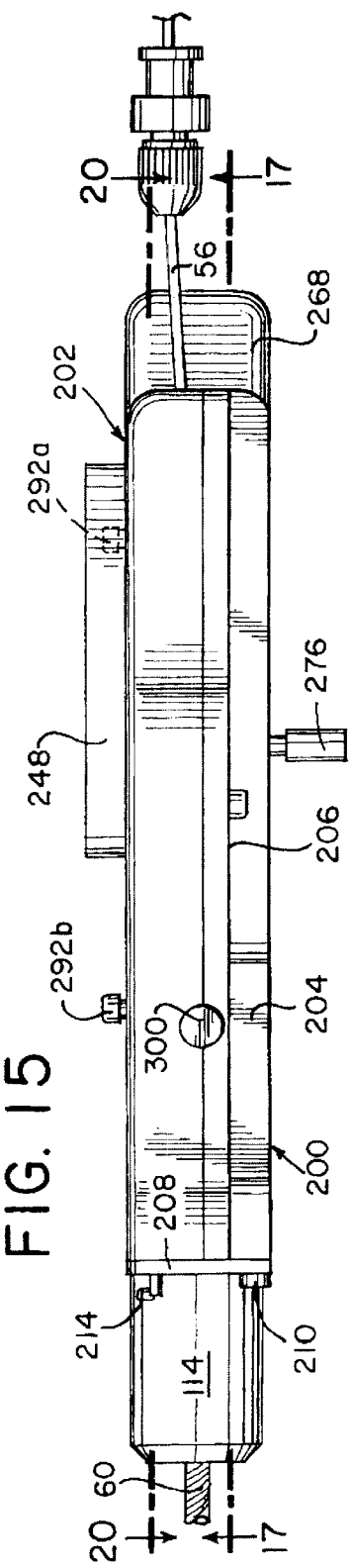
FIG. 15 is a top view of an actuator subassembly and a catheter mounting subassembly in assembled relationship to one another for remotely controlling the deployment head of the present invention.
Figure 22:
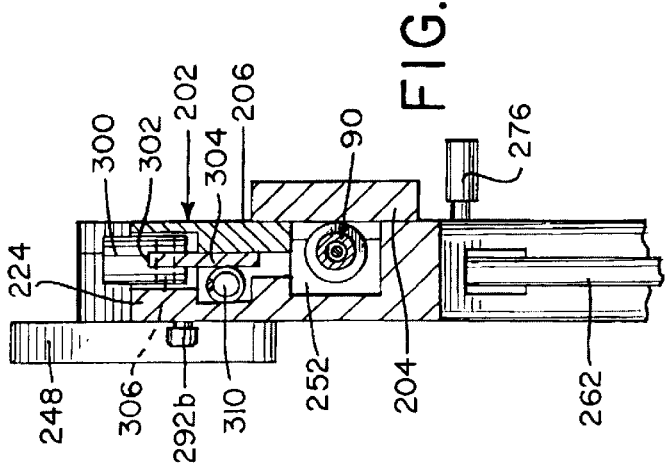
FIG. 22 is a cross-section taken along the line 22—22 of FIG. 17 showing the catheter mounting subassembly and the actuator subassembly in engaging relationship to one another.
Figure 16:
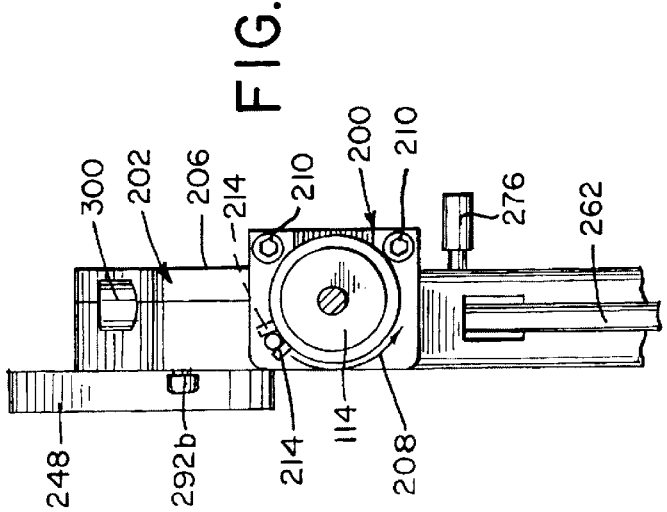
FIG. 16 is a front view of the assembly of FIG. 15.
Figure 17:
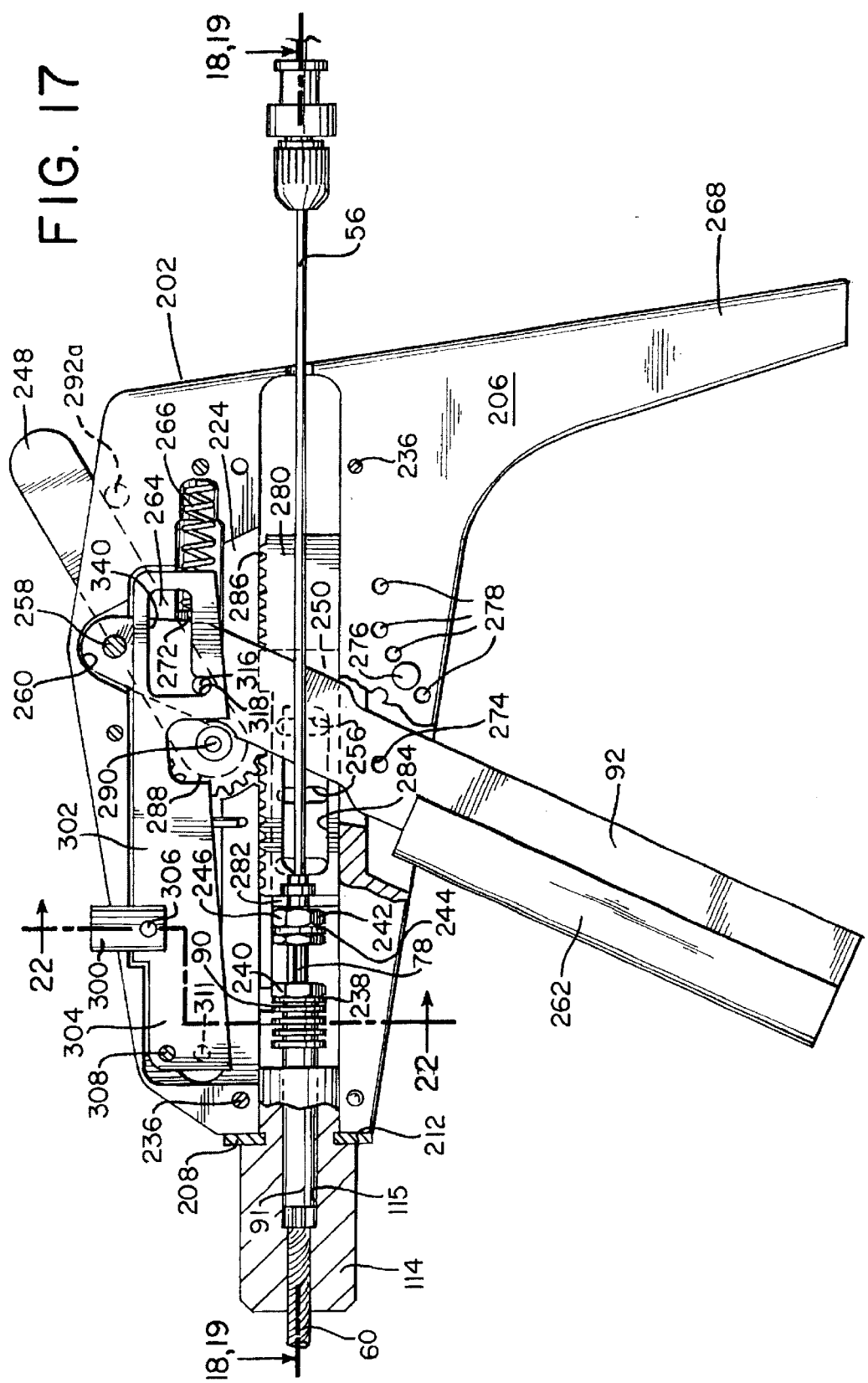
FIG. 17 is a partial cross-section of one side of the assembly taken substantially along line 17—17 of FIG. 15.
Figure 21:
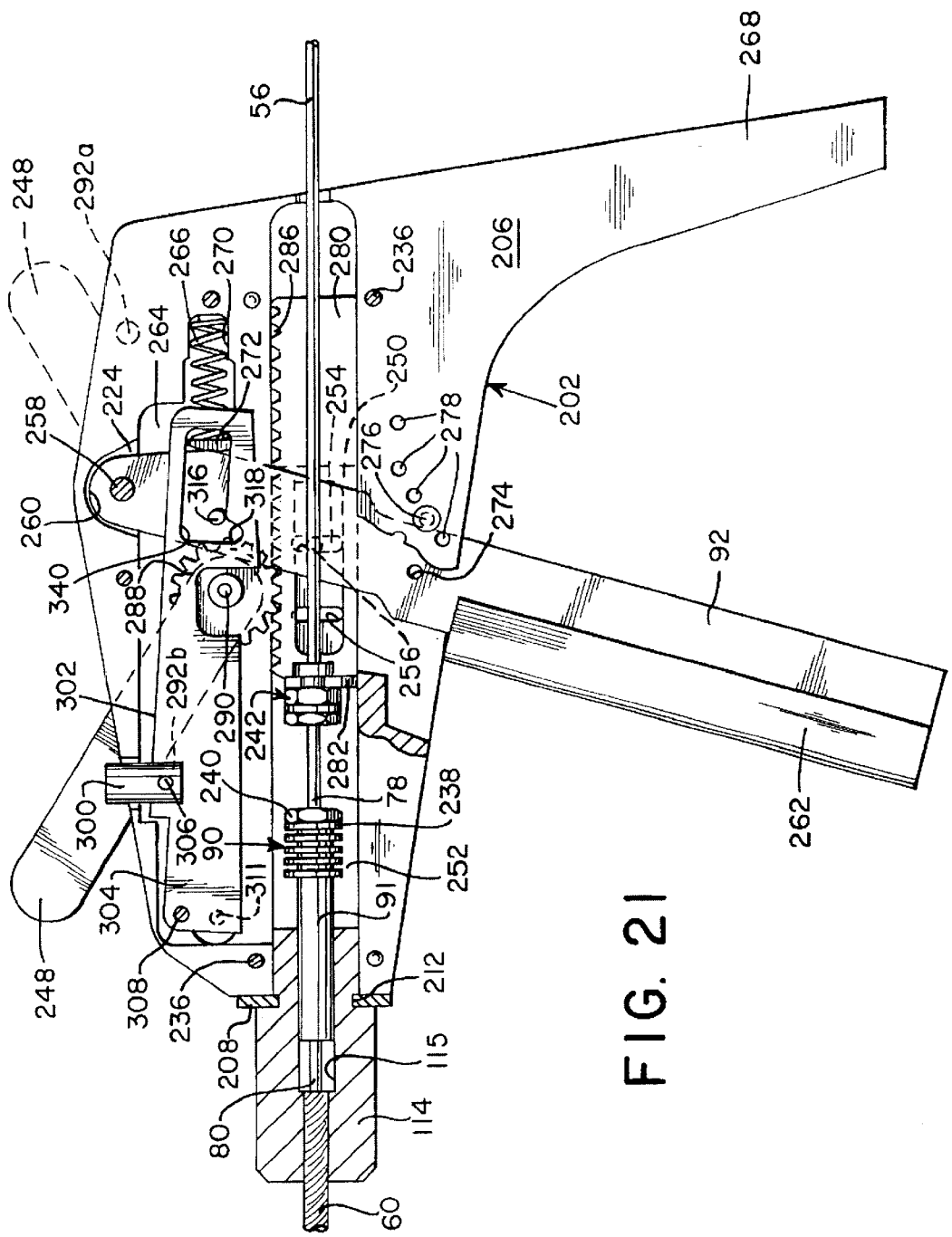
FIG. 21 is the same view as FIG. 17 showing the operation of a trigger and an actuating lever.
Figure 23:
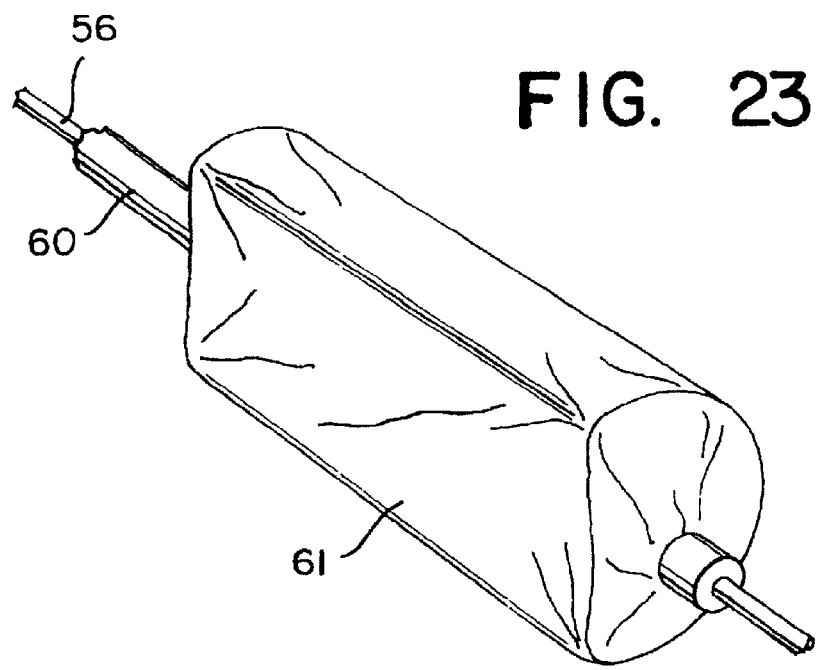
FIG. 23 is a perspective view of the distal end of a catheter which supports a preshaped balloon.
Figure 24:
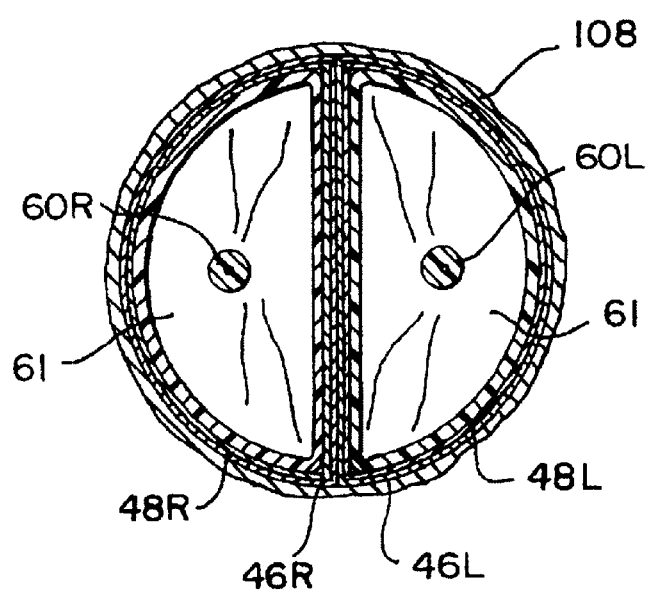
FIG. 24 is a cross-section as in FIG. 6, showing the preshaped balloon of FIG. 23.

Each control mechanism comprises a catheter mounting subassembly 200 and an actuator subassembly 202 (FIGS. 15 and 17). The catheter mounting subassembly comprises a plate 204 that supports the rotatable nose cone 114, a multiply ribbed anchor 90 attached to the proximal end of the deployment wire 80, and an anchor 242 attached to the proximal end of the initiator wire 78 (FIG. 21). The catheter mounting subassembly mates with a first side 206 of the actuator subassembly 202 to form an assembled control mechanism 54. A C-shaped retaining ring 208 is attached to the proximal end of the plate 204 by a pair of screws 210 to unite the mounting subassembly 200 with the nose cone 114. The nose cone has a circumferential groove 212 (see FIG. 17) that permits it to be rotatably supported in the retaining ring 208 to the plate 204. It is desirable to have the nose cone rotatably supported in the catheter mounting subassembly so that the head 50 can be rotated once located within a patient's body for redistending the stent at contact points other than where the stent is first distended. The nose cone is provided with a stop 214, as shown in FIG. 16, that limits rotation to approximately 360°. A click stop (not shown) may be provided at regular intervals, for example, 45°, to provide a tactile indication of the amount of rotation brought about by rotation of the nose cone 114. The multiply ribbed anchor 90 has at its distal end a cylindrical sleeve 91 that is slideably mounted in an annular recess 115 in the proximal face of the nose cone 114.

Because the control mechanisms for each deployment head 50L,R are identical, only one control mechanism 54 is described.

FIGS. 18 and 19 show cross-sections of the mounting subassembly and the actuator subassembly before and after the control mechanism 54 is assembled, respectively. Assembly is facilitated by a peg 234 and a hole 232 complementarily formed on each of the mounting subassembly and the actuator subassembly, as shown in FIG. 18, to guide the catheter mounting subassembly and the actuator subassembly together. The shaft 60 is received in the control mechanism 54 by means of the catheter mounting subassembly 200 after the graftstent complex 44 has been loaded upon the shaft 60 and delivered to the desired location within a patient's vascular system. The mounting subassembly 200 is then secured to the actuator subassembly 202 to form a single mechanism as by the screws 236, shown in FIG. 17, or by any other means to hold two components together. The mounting subassembly enables each head 50L,R to be operated remotely by a respective trigger 92L,R, yet further provides an automatic calibration of the distention of the stent, as described below.

Advantageously, the travel of triggers 92 is calibrated to the radial motion of the wings so that dilation of the stent is certain and precise. The deployment wire 80, which is coupled at its distal end to the tubular slide 86, is rigidly coupled at its proximal end to the anchor 90 by a washer 238 and a nut 240 (see FIG. 17) so that a force applied to the anchor 90 by the trigger 92 is conveyed to the tubular slide 86 to displace the wings and distend any stent thereon. In similar manner, the initiator wire 78 coupled at its distal end to the initiator 88 is coupled at its proximal end to a spool-shaped anchor 242 by a washer 244 and a nut 246. A force applied to the anchor 242 by the actuating lever 248 is thus conveyed to the initiator 88 to displace the wings slightly radially outward, as described above in connection with FIG. 8. Thus, proximal motion of the initiator 88 causes the wings 52a,b,c,d to be slightly radially displaced.

With further reference to FIGS. 18 through 20 and 22, the trigger 92 is shown coupled to the anchor 90 by a slotted yoke slide 250 terminated at the distal end in a yoke 252. The yoke 252 selectively engages multiply ribbed the anchor 90 between any one of several ribs when the catheter mounting subassembly is assembled with the actuator subassembly (see FIG. 22). This is a self-zeroing control to account for cable bending, as more completely described in connection with the operation of the device. Thus, the actual set of ribs on the anchor 90 to which the yoke 252 engages is determined based on the orientation of the shaft 60 in the patient's body. This ensures that the yoke 252 engages the anchor 90 with the wings completely recoiled to provide the most compact profile achievable, yet permit the wings to maintain a calibrated position relative to the trigger 92. A link pin 254 attached to the trigger engages one of a plurality of vertical slots 256 in the yoke slide 250 so that the travel of the trigger remains accurately calibrated to the force conveyed to anchor 90 which, in turn, governs the radial displacement or recoil of the wings. The trigger pivots on a pin 258 in an arcuate shaped milled recess 260 formed in the second side 224 of the actuator subassembly 202. As the trigger pivots on the pin 258, the link pin 254 travels in an arc along with the trigger. The link pin 254 draws the yoke slide 250 linearly forwards and backwards in the actuator subassembly 202 by engagement with the vertical slots 256. The vertical slots 256 accommodate the arc traced by the link pin 254 as it travels with the trigger while translating the pivotal motion of the trigger into the linear motion of the yoke slide 250. This pivotal motion is in response to a force applied to a grasp handle 262 which may be provided to ensure a firm control over the trigger.

In operation, once each head 50 has been advanced to the designated site, the shaft 60 will likely have bends in it between its distal and proximal ends. These bends will pull on the initiator and the deployment wires 78,80 which in turn will axially reposition the anchors 90,242 with respect to the nose cone 114 at the proximal end of the shaft 60. The degree of tortuosity typically is unique to each iliac branch and so the degree of bending of each the shaft 60 will likely be different. Nevertheless, the calibration of the holes 278

(see FIG. 17) remains intact because the deployment anchor 90 always engages the yoke 252 with the wings 52 in a completely recoiled stance when the catheter mounting subassembly is joined with the actuator subassembly. This is due to the multiply ribbed surface of the anchor 90 which engages the yoke 252 regardless of its axial position relative to the yoke 252 at the moment when the subassemblies are joined. In effect, this provides a built-in self-zeroing feature so that regardless of the tortuosity of the vasculature, each head 50 will be in its closed position when the stent is properly located.

Between the trigger and the yoke slide 250 is a rack 280 terminated at one end with a yoke 282. Rack 280 has an aperture 284 so that it can slide in the actuator subassembly 202 without contacting the pin 254 of the trigger 92. The rack 280 has on a top margin thereof a set of teeth 286 that cooperate with a pinion gear 288 formed on one end of actuating lever 248. The actuating lever 248 pivots about a pin 290 between a pair of lever stops 292a,b (see FIG. 15). From FIGS. 20 and 21, it is seen that as the actuating lever 248 pivots from 292a to 292b, the pinion gear 288 drives the rack 280 in an opposite direction and tows the anchor 242 therealong.

An edge 264 of the trigger 92 is normally biased by a spring 266 into a forward position, away from a butt 268 of the actuator subassembly. The spring 266 is housed in a horizontal slot 270 and urges a disc 272 against the edge 264 in resistance to any force applied to the trigger. As part of a safety mechanism, the trigger 92 may include an aperture 274 for receiving a peg 276 from a corresponding hole in the actuator subassembly 202. The peg 276 restrains the trigger from pivotal motion until removed from the aperture 274. A set of peg holes 278 extending toward the butt 268 is shown for limiting the motion of the trigger to the hole in which the peg 276 has been placed. Advantageously, each of the holes 278 is calibrated to the relative displacement of the wings so that the holes 278 may be labeled, for example, 20, 24, 26, 28, 30, and so on, to provide a millimeter scale of the distention of the stent upon squeezing the trigger to a particular one of the holes 278.

Figure 20:
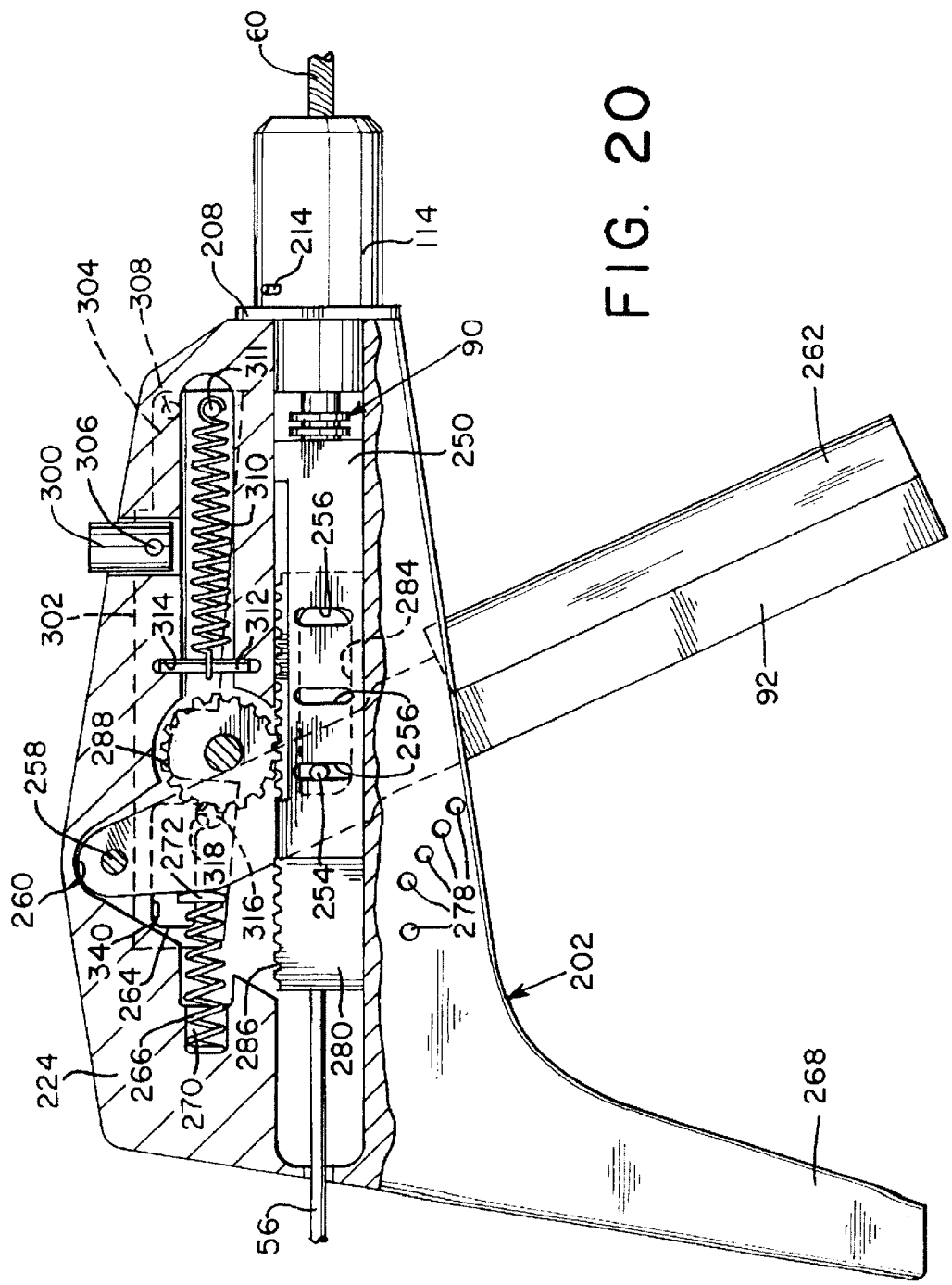
FIG. 20 is a partial cross-section of a second side of the actuator subassembly and the catheter mounting subassembly taken substantially along line 20—20 of FIG. 15.

The control mechanism 54 includes a trigger lock mechanism that restrains the trigger from pivotal motion unless a button 300 on a top surface 302 of the control mechanism is first depressed. This button is attached to a lever lock 304 by a pivot 306 (FIGS. 20 and 21). The lever lock 304 pivots about a pivot pin 308 and is normally biased by a spring 310 into a locked position (see FIGS. 17 and 22). The spring 310 is connected between a pin 311 below the pivot pin 308 on the lever lock 304 and a post 312 disposed in a pair of slots 314 formed in the actuator subassembly 202. A pin 316 (FIGS. 17 and 21) on the trigger 92 rests in a slot 318 formed in the lever lock 304 when lever lock is in its locked position. So long as the pin 316 is in the slot 318 (FIGS. 17 and 20), the trigger cannot pivot and the wings will remain in a recoiled position. When the button is depressed, however, the lever lock pivots about the pivot pin 308 and releases the trigger pin 316 from the slot 318. With the trigger pin released, it can travel freely within an aperture 340 formed in the lever lock 304 while the trigger is being squeezed. Thus, the trigger 92 radially displaces the wings 52a,b by the coupling of the trigger to the wings 52a,b by way of the link pin 316, the slotted yoke slide 250, the yoke 252, the multiply ribbed anchor 90, the deployment wire 80, the tubular slide 86, and the coupling arms 82.

By means of an angiogram and a CT scan the operator can determine the length of the aneurysm and obtain an indication of the lumen width in the region surrounding the aneurysm. This indication of lumen width is advantageously used to set the maximum travel of the trigger 92 by setting the peg 276 in an appropriate one of the calibrated holes 278. Once the amount of distention is known, a suitable stent or graftstent complex may be selected. The entire graftstent 44 can be prefabricated and mounted on the head 50 in a manner ready for connection to the actuator subassembly 202 and subsequent deployment; a surgeon need only specify the length of the graft 46 necessary to bypass an aneurysm and the maximum distention desired of the stents 48L,R.

In operation, the actuating lever 248 is advanced from the lever stop 292a to 292b to draw the initiator 88 toward the annular support 59 and to separate the wings slightly radially. The trigger lock button 300 can then be released and the trigger 92 compressed toward the butt 268 to draw the tubular slide 86 toward the annular support 59 and displace the wings 52a,b. As the wings 52a,b displace radially outward, the distance between each wing increases and the stent, supported on the wings, assumes a radially expanded circumstance in a "D" shaped configuration. The trigger 92 may be squeezed until it hits the peg 276 (FIG. 21). At that point, the stents 48L,R may be expanded sufficiently to anchor them to the body lumen 108 and to each other by friction. When a barbed stent is used, the stents 48L,R engage each other through the graft material 46L,R more securely. Either of the stents 48L,R can be incrementally dilated to a larger size by removing the peg 276 and squeezing the trigger 92 beyond the hole 278 that the peg 276 formerly occupied. This may be done on a moment-by-moment basis depending on real time fluoroscopic images and the operator's discretion as a function of the actual arterial dimensions. When the trigger is released, the spring 266 urges the trigger to its rest position which conveys a pushing force through the yoke 252 and the deployment wires 80 to the tubular slide 86. When the tubular slide 86 is pushed away from the annular support 59, the wings return to a radially recoiled stance and the stents 48L,R retain their radially expanded "D" shaped configuration.

Figure 14:
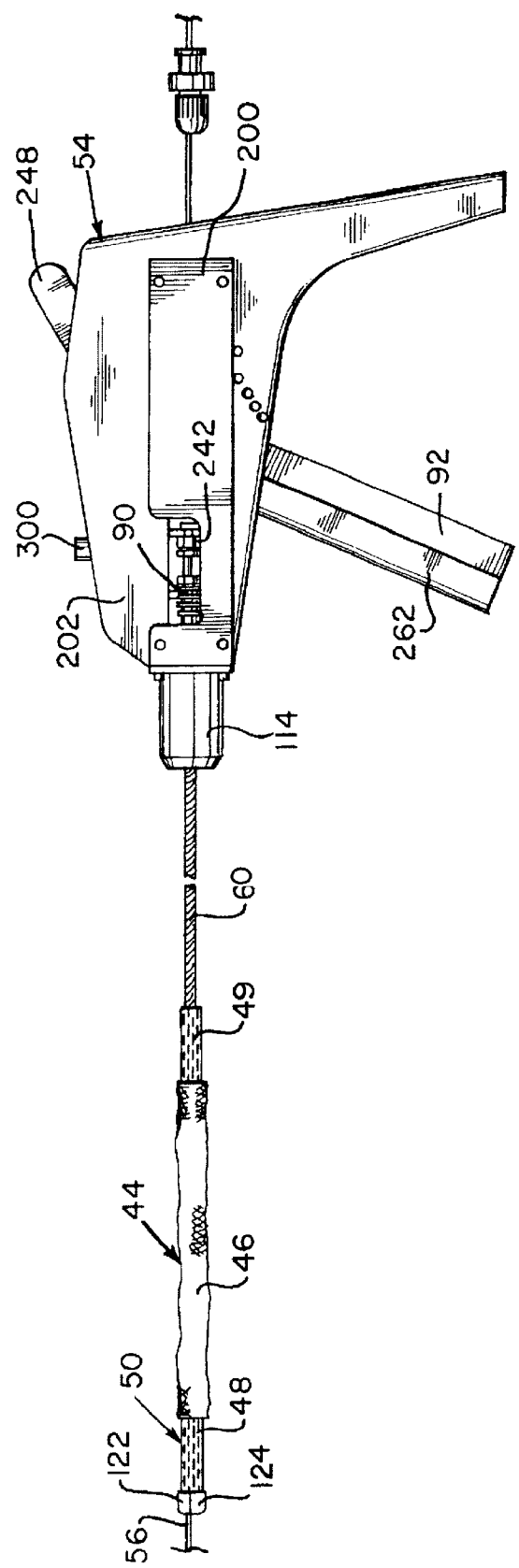
FIG. 14 is a side view of a prosthesis mounted on an apparatus as may be used with the method of the present invention.

To rotationally align the collateral stents 48 on each deployment head 50, the nose cone 114 is rotated until the markers 115 face each other (see FIG. 14). Rotation of the nose cone 114 faithfully turns the shaft 60 and the head 50 at the distal end of the shaft in substantially a one-to-one ratio, thereby rotating one of heads 50L,R with respect to the other within the body lumen 108. Once the stents 48L,R are rotationally aligned, the trigger 92 is squeezed to distend the wings 52.

The position of the caudal stents 49L,R are preferably adjusted prior to their deployment. Adjustment of each caudal stent 49 may be accomplished by withdrawing a respective deployment head 50L,R until it is just proximal to either of (caudal) stents 49L,R. This may be accomplished with the assistance of a fluoroscopic image of the patient's abdominal cavity. Once the deployment heads 50 have been withdrawn to this position, expansion of the wings 52 is initiated using the actuating lever 248. The heads 50 form a shelf to support the proximal margin of stents 49L,R. The heads 50 can then be slowly advanced distally (cephalically) to engage the proximal margin of each stent 49, as illustrated in FIG. 4. With deployment head 50 in a partially expanded state, wings 52 can urge the stent 49 into position while the stent is still within a respective guidesheath 58L,R. This may be necessary when stent 49 would otherwise block the mouth of the internal iliac artery (point F). Once each caudal stent 49L,R is located in an appropriate position, the deployment head 50L,R is held in position while guidesheath 58L,R is withdrawn proximally (caudally). In this manner, head 50 provides a shelf-like surface to restrain proximal (caudal) movement of the caudal stent while the caudal stent 49 is permitted to return to its naturally expanded tubular form. Once expanded, the stent 49 frictionally engages the body lumen 108 within a common iliac artery. The graft material 46 is sewn or otherwise attached to the distal (cephalic) margin of the stent 49 to complete the graftstent complex 44 (which, in this example, comprises the stent 48, the graft material 46, and the stent 49). As noted above, where the head 50 is formed of plastic or epoxy materials, it is advantageously provided with a radiopaque portion to assist in the fluoroscopic alignment process.

The direct transmission of a physical force from the trigger 92 to the head 50 permits rapid displacement and recoil of the wings. Displacement and recoil can be performed in virtually less than a second, as compared to the time required for balloon dilatation which, in the case of relatively large balloons with conventionally sized inflation lumens, may be as much as twenty to thirty seconds and sometimes up to a minute. Relative to balloon based devices, therefore, the present invention operates substantially instantaneously without the delays associated with filling and emptying a balloon. All the while, intraluminal fluids flow between the radially displaced wings to the vasculature in the region of the device deployment.

Each of wires 78 and 80 is preferably stainless steel. The head 50 may be produced in a disposable or non-disposable fashion. Where the head 50 is to be disposed of after usage, at least the wings 52, the tubular slide 86, the coupling arms 82,83,84, the initiator 88, and the annular support 59 may be compression molded or extruded from an epoxy material or plastic. The same components of the head 50 listed above are advantageously formed of stainless steel where the head 50 is intended to be reused in a subsequent procedure. One skilled in the art would recognize that the choice of materials for the head affects the radiopacity of the head. Thus, an epoxy or plastic head would be radiolucid as compared to a stainless steel head which would be radiopaque.

The guidesheath 58 may be of a plastic or teflon material. Presently, the materials most commonly used as prosthetic arterial grafts are PTFE ("GORTEX"), expanded PTFE, and polyester ("DACRON"), however, other suitable grafts may be used with this device. No single prosthetic material has surfaced as being superior to others. Excellent results may also be achieved using a patient's own accessory vein, albeit with more imposition to the patient.

The invention is intended for use in deploying stents and attachment devices, i.e., devices which may be attached to a body lumen such as an artery, for example to secure a graft in place, in the vicinity of a vasculature bifurcation. As used herein, the term "stent" is intended to also include such attachment devices. The invention can be used with any radially expandable stent, including stents that are partially self-expanding.

While the foregoing description has been directed primarily to abdominal aortic aneurysms, which is the best mode contemplated, the invention has application in other portions of the vasculature, such as where a segment of arterial tissue in the vicinity of a vasculature bifurcation must be bypassed. By way of example, this may be at the aortic artery bifurcation, at the iliac artery bifurcation, and at the innominate artery bifurcation.

Further, the invention has application in body passageways other than arteries which branch from a common passageway and require treatment in the vicinity of the branching passageways. For example, the invention has utility in the treatment of tracheal esophageal fistulae when the deployment heads 50 are introduced through a patient's mouth to isolate a pathological connection. The trachea and esophagus may be isolated by deploying on one side of the pathological connection the stents 49L,R of the graftstent complexes 44 in the left and right bronchi and deploying the stents 48L,R in the trachea on the other side. Similarly, a malignant obstruction in the trachea, for example, a cancer, may be excluded from the windpipe by deploying graftstent complexes 44 as previously described. As another example, the invention may be used to treat a stenosis or injury, for example, a hole, in the left or right ureter, by introducing the deployment heads 50L,R through the urethra and deploying the stents 49L,R at one end of the graftstent complexes 44 in a respective one of the left and right ureters and the stents 48L,R at the other end within the urinary bladder. These examples are illustrative, and not exhaustive, of the many passageways in which the invention may be utilized.

Of course, the portion of the graftstent complexes 44 that extend into branched passageways may be attached in the branched passageways prior to aligning and attaching the stents in a common passageway. Such a procedure is appropriate when the operator enters the body passageway at a location more proximal to the common passageway. Hence, when an operator cannulates the thoracic aorta as a method of gaining access to the aortic aneurysm 40, the caudal portion of each graftstent complex 44L,R is positioned within a respective one of the iliac arteries before the stents 48L,R are aligned and deployed. If the graftstent complexes 44 include the caudal stents 49L,R, then these stents are deployed or expanded in the iliac arteries prior to aligning and deploying the stents 48L,R. Further, with reference to the foregoing exemplary applications, it is contemplated that the caudal portions of the graftstent complexes 44 are positioned and deployed before positioning and deploying the cephalic stents 48L,R in the treatment of tracheal esophageal fistulae, malignant tracheal obstructions, and ureteral dysfunctions.

Hence, when the operator enters a body passageway from a common passageway, the pathological defect is isolated by advancing a pair of graftstent complexes, which have been previously loaded on catheter devices, along a pair of guidewires which have been previously positioned in branched passageways which communicate with the common passageway. The graftstent complexes include at least a stent and a portion of graft material; however, it is preferred that the graftstent complexes include a pair of stents 48,49, one connected to each end of the graft.

When two stents are provided for each graftstent complex, a first stent (here 49L,R) is deployed in each of the branched passageways to secure the graftstent complexes on one side of the pathological defect within the branched passageways. The stents may be positioned, for example, so as to not stretch across the ostium of another passageway branching from the branched passageway, or so as to extend beyond the pathological defect to one side of the defect. This may be accomplished as described above in connection with FIG. 4. When present, the first stents are preferably of the self expanding variety, that is, they are mechanically or thermally activated, so that when guidesheath 58 is withdrawn, the stents expand into contact with the body passageway.

The second stents of the graftstent complexes may be aligned within the common passageway, as through the use of markers, as previously described. Preferably, the second stents are coaxially positioned on the deployment heads 50L,R by withdrawing each deployment head 50L,R until the second stents pass over the secondary rib 124 of each wing 52. It is preferred that the second stents (here stents 48L,R) have an inside diameter that is greater than the diameter of the wings 52 at the radial cross-section of the secondary rib 124, yet less than the diameter of the wings 52 at the radial cross-section of the primary rib 122 (see FIG. 7), so that the second stents can readily be mounted on the wings 52. However, radiopaque or other markers can be used instead, or in addition, to ascertain whether the second stents have been coaxially positioned over the deployment member.

Once aligned, these second stent are deployed on another side of the pathological defect so as to isolate fluid flow in the passageway from natural tissue. As a result of the procedure, the graftstent complex is secured across the pathological defect within the common and branched body passageways. The pathological defect may be, for example, an aneurysm or an occlusion such as a cancer.

While the foregoing is a preferable mode of introducing a graftstent complex from a common passageway, other configurations are possible. For example, if a graftstent complex is introduced through a common passageway and advanced toward branched passageways of the type in which fluid flows from in the direction of the branched passageways, for example, from the aorta to the iliac arteries, then the fluid flow, for example, blood, will naturally carry the graft over the guidewire and into position, without the need for a stent to be deployed in the branched passageways, nor the need for withdrawing a stent deployment means from the branched passageways. All that is required in this alternative configuration is that the graft be selected of a material and sidewall construction that resists collapsing and twisting.

The "term" fluid as used herein is meant to embrace any gas that flows, for example, air.

Although the invention is shown with one head deploying a single stent at a time, it is contemplated that two heads on a single device may simultaneously deploy two spaced apart stents.

From the foregoing description, it will be clear that the present invention may be embodied in other specific forms without departing from the spirit or essential characteristics thereof. The presently disclosed embodiments are therefore to be considered in all respects as illustrative and not restrictive, the scope of the invention being indicated by the appended claims, and not limited to the foregoing description.

We claim:

1. An intraluminal delivery system, comprising:
  a delivery sheath;
  an expansion catheter having a radially-expandable element, the expansion catheter being slidably positioned within the delivery sheath; and
  a graftstent complex which includes a mechanically-expandable stent, a self-expanding stent and a graft connected between the stents, the mechanically-expandable stent being supported on the radially-expandable element while the graft and self-expanding stent are seated proximal to the radially-expandable element and within the delivery sheath,
  wherein the graft is a prosthetic material selected from the group consisting of PTFE, expanded PTFE, and polyester.

2. A method for endoluminally excluding an aortic aneurysm in a patient's vascular system, comprising the steps of:
  advancing through each branch of the patient's femoral and iliac system a respective graftstent complex, each graftstent complex comprising a first stent, a second stent and a graft connected to said first and second stents and extending therebetween, said graft being a prosthetic material selected from the group consisting of PTFE, expanded PTFE, and polyester and said second stent being a self-expanding stent;
  positioning said first stents relative to each other in a common region of normal aortic tissue on one side of the aneurysm;
  deploying each of said positioned first stents in the common region; and
  deploying each of said second stents in the iliac arteries.

3. The method as in claim 2, wherein each graftstent complex is advanced within a delivery catheter.

4. The method as in claim 3, wherein said delivery catheter includes a guidesheath.

5. The method as in claim 4, including wherein said second stents are deployed upon retraction of the guidesheath.

6. The method as in claim 2, wherein the step of deploying said second stents comprises maintaining the position of the second stents relative to the patient's vasculature while withdrawing the guidesheath proximally.

7. A method for endoluminally excluding an aortic aneurysm in a patient's vascular system, comprising the steps of:
  advancing through each branch of the patient's femoral and iliac system a respective graftstent complex, each graftstent complex comprising a first stent, a second stent and a graft connected between said first and second stents, said first stent having at least one barb for securing the position of the first stent within the patient's vascular system said graft being a prosthetic material selected from the group consisting of PTFE, expanded PTFE, and polyester;
  positioning said first stents relative to each other in a common region of normal aortic tissue on one side of the aneurysm;
  deploying each of said positioned first stents in the common region; and
  deploying each of said second stents in the iliac arteries.

* * * * *